(12) United States Patent
Catanzariti et al.

(10) Patent No.: US 6,528,632 B1
(45) Date of Patent: Mar. 4, 2003

(54) NUCLEIC ACID ASSAYS

(75) Inventors: Luigi Catanzariti, Duxbury, MA (US); Bryan W. Kluttz, Norwell, MA (US); Marcela Vera-Garcia, Framingham, MA (US); J. Lawrence Burg, Framingham, MA (US); James G. Moe, Franklin, MA (US); Geoff A. McKinley, Duxbury, MA (US)

(73) Assignee: bioMerieux Vitek, Hazelwood, MO (US)

(*) Notice: Subject to any disclaimer, the term of this patent is extended or adjusted under 35 U.S.C. 154(b) by 0 days.

(21) Appl. No.: 09/586,546

(22) Filed: May 31, 2000

Related U.S. Application Data

(63) Continuation of application No. 08/850,171, filed on May 2, 1997, now abandoned.

(51) Int. Cl.⁷ ............................ C07H 21/02; C12P 19/34
(52) U.S. Cl. ........................................ 536/23.1; 435/91.2
(58) Field of Search ............................. 435/5, 6, 91.2; 536/22.1

(56) References Cited

U.S. PATENT DOCUMENTS

| | | | | |
|---|---|---|---|---|
| 4,457,916 | A | 7/1984 | Hayashi et al. | 424/101 |
| 4,581,333 | A | 4/1986 | Kourilskey et al. | 436/6 |
| 4,762,857 | A | 8/1988 | Bollin, Jr. et al. | 514/777 |
| 4,891,319 | A | 1/1990 | Roser et al. | 435/188 |
| 5,026,566 | A | 6/1991 | Roser et al. | 426/443 |
| 5,098,893 | A | 3/1992 | Franks et al. | 514/54 |
| 5,122,284 | A | 6/1992 | Braynin et al. | 210/782 |
| 5,229,297 | A | 7/1993 | Schnipelsky | 436/94 |
| 5,432,271 | A | 7/1995 | Barns et al. | 536/24.32 |
| 5,437,990 | A | 8/1995 | Burg et al. | 435/91.7 |
| 5,457,027 | A | 10/1995 | Nadeau et al. | 435/6 |
| 5,489,653 | A | 2/1996 | Charles et al. | 525/327.5 |
| 5,498,392 | A | 3/1996 | Wilding et al. | |
| 5,510,084 | A | 4/1996 | Cros et al. | 422/104 |
| 5,521,300 | A | 5/1996 | Shah et al. | 536/24.32 |
| 5,541,308 | A | 7/1996 | Hogan et al. | 536/23.1 |
| 5,554,516 | A | 9/1996 | Kacian et al. | 435/91.21 |
| 5,587,128 | A | 12/1996 | Wilding et al. | |
| 5,589,585 | A | 12/1996 | Mabilat et al. | 536/24.32 |
| 5,645,801 | A | 7/1997 | Bouma et al. | |
| 5,693,468 | A | 12/1997 | Hogan et al. | 435/6 |
| 5,703,217 | A | 12/1997 | Mabilat et al. | 536/23.1 |
| 5,710,029 | A | 1/1998 | Ryder et al. | 435/6 |
| 5,712,385 | A | 1/1998 | McDonough et al. | 536/24.32 |
| 5,747,252 | A | 5/1998 | Yang et al. | 435/6 |
| 5,766,849 | A | 6/1998 | McDonough et al. | 435/6 |
| 5,780,273 | A | 7/1998 | Burg | |
| 5,807,717 | A * | 9/1998 | Joyce | 435/91.1 |
| 5,849,901 | A | 12/1998 | Mabilat et al. | 536/23.7 |
| 5,856,088 | A | 1/1999 | McDonough et al. | 435/5 |
| 5,871,975 | A | 2/1999 | Kacian et al. | 435/91.2 |
| 5,908,744 | A | 6/1999 | McAllister et al. | 435/6 |
| 6,136,529 | A | 10/2000 | Hammond | 435/6 |

FOREIGN PATENT DOCUMENTS

| | | |
|---|---|---|
| DE | 195 03 685 A | 1/1996 |
| DE | 195 03 685 | 8/1996 |
| EP | 0428693 B1 | 4/1993 |
| EP | 0 622 464 | 3/1994 |
| EP | 0 623 682 | 4/1994 |
| EP | 0726 310 A1 | 2/1996 |
| EP | 0 726 310 A1 * | 8/1996 |
| EP | 0732408 A2 | 8/1996 |
| WO | WO 87 00196 | 1/1987 |
| WO | WO 89 00012 | 1/1989 |
| WO | WO 89 00290 | 1/1989 |
| WO | WO 89 06542 | 7/1989 |
| WO | WO 93 00806 | 1/1993 |
| WO | WO 93 21346 | 10/1993 |
| WO | WO 95 33488 | 12/1995 |

OTHER PUBLICATIONS

P. Allibert, et al. (1992) "Automated Detection of Nucleic Acid Sequences of HPV 16, 18 and 6/11," *RBM*, 14.3, p. 152–155.

Mabilat, et al. "Routine Identification of Mycobacterium Tuberculosis Complex Isolates by Automated Hybridization", *Journal of Clinical Microbiology*, vol. 32, No. 11, Nov. 1994, p. 2702–2705.

Ramanujam et al. (1993) "Ambient–Temperature–Stable Molecular Biology Reagents" *Biotechniques* 14(3): 470–472, 474–475.

Colaco et al.,(1992) "Extraordinary Stability of Enzymes Dried in Trehalose: Simplified Molecular Biology" *Bio/Technology* 12: 1007–1011.

Franks (1994) "Long–Term Stabilization of Biologicals" *Bio/Technology* 12:253–256.

Hermanson (1996) *Bioconjugate Techniques* (Academic Press, San Diego) pp. 666–667.

Uredea et al. (1988) "A Comparison of non–radioisotopic hybridization assay methods using fluorescent, chemiluminescent and enzyme labled synthetic oligodeoxyribonucleotide probes" *Nucleic Acids Research* 16(11): 4937–56.

English Translation for DE 195 03 685 A1.

European Search Report in Corresponding European application, dated Oct. 23, 2001.

English Abstract for DE 195 03 685 A1.

* cited by examiner

*Primary Examiner*—Jeffrey Fredman
*Assistant Examiner*—Prabha Chunduru
(74) *Attorney, Agent, or Firm*—McDonnell Boehnen Hulbert & Berghoff

(57) ABSTRACT

The present invention relates to the detection of specific nucleic acid sequences after an amplification process, or directly without amplification. In particular, the invention provides for the automation of the amplification and detection process, the amplification and detection of one or more specific nucleic acid sequences, the use of internal controls, reduced potential for contamination caused by the manual manipulation of reagents, and improved reagent compositions to better control assay performance and provide for further protection against contamination.

2 Claims, 30 Drawing Sheets

FIG. 23A

```
2.22 T  2.74 T
2.00 T  2.03 T
3.04 C  1.68 A
1.95 A  3.87 C    RAND()*4
1.59 A  2.01 T    IF(AND(0<A1,A1<1),"G",IF(AND(1<A1,A1<2),"A",IF
3.65 C  2.72 T    (AND(2<A1,A1<3),"T",IF(AND(3<A1,A1<4),"C","Oops"))))
0.25 G  1.07 A
3.47 C  2.11 T
3.24 C  1.09 A
0.56 G  3.69 C
0.68 G  2.41 T
0.07 G  0.18 G
0.87 G  3.18 C
2.98 T  3.80 C
3.02 C  2.28 T
1.09 A  0.65 G
0.28 G  3.42 C
1.49 A  3.01 C
0.51 G  2.71 T
2.06 T  3.91 C
1.42 A  2.24 T
1.52 A
1.42 A
0.79 G
0.31 G
1.24 A
1.63 A
```

| | | | | | | | | | | | | | | | | | | |
|---|---|---|---|---|---|---|---|---|---|---|---|---|---|---|---|---|---|---|
| RAN1  | G | C | A | G | G | T | C | T | G | C | T | C | C | C | G | A | G | C | C |
| RAN2  | T | A | T | T | A | C | G | A | C | C | A | T | T | A | T | A | C | A | T |
| RAN3  | G | G | G | A | C | G | T | T | C | A | A | A | C | C | G | T | T | A | A |
| RAN4  | A | C | G | C | T | A | A | C | A | A | G | T | A | C | T | A | T | T | A |
| RAN5  | A | C | T | T | A | T | A | C | C | A | T | T | T | A | A | T | G | A | G |
| RAN6  | T | A | T | A | A | A | T | G | A | C | G | G | C | A | T | A | A | A | G |
| RAN7  | C | C | C | C | C | G | G | C | G | C | T | G | C | C | A | G | G | T | G |
| RAN8  | T | G | T | T | G | A | C | T | A | A | C | C | A | A | A | A | A | T | T |
| RAN9  | T | C | G | G | T | T | G | A | G | C | A | G | G | A | G | A | A | A | A |
| RAN10 | T | A | C | T | G | A | T | G | G | A | T | G | C | C | G | A | T | G | A |
| RAN11 | C | T | G | C | C | G | A | T | T | T | G | G | A | G | C | C | T | G | C |
| RAN12 | A | A | G | T | T | A | C | T | A | G | T | A | A | C | C | C | C | A | G |
| RAN13 | T | C | C | A | A | T | A | T | T | G | A | A | C | T | T | C | C | A | G |
| RAN14 | C | A | A | C | T | T | T | C | G | C | C | C | A | G | C | C | T | G | A |
| RAN15 | C | T | C | T | A | C | A | A | T | C | A | A | G | G | C | C | G | G | A |
| RAN16 | A | G | C | G | A | A | T | G | T | T | A | A | G | G | G | C | A | T | C |
| RAN17 | A | C | C | C | G | C | A | A | A | G | G | T | T | G | G | C | G | T | C |
| RAN18 | T | T | C | A | C | A | A | C | A | G | T | A | C | T | T | G | C | T | A |
| RAN19 | T | C | T | G | G | T | C | G | T | C | A | A | T | G | C | C | T | T | T |
| RAN20 | G | A | T | T | A | A | T | A | T | C | C | G | G | G | T | T | G | A | C |
| RAN21 | T | A | A | G | G | G | C | T | G | A | T | G | T | C | A | G | G | A | T |
| RAN22 | A | A | C | C | G | C | G | A | A | C | G | G | G | T | T | C | A | G | G |
| RAN23 | G | T | T | A | C | T | T | T | C | T | G | C | T | G | T | T | G | A | G |
| RAN24 | A | C | T | A | G | A | A | C | G | G | A | A | C | C | T | T | A | A | G |
| RAN25 | G | A | G | G | A | T | C | T | T | A | C | A | A | A | T | C | G | A | G |
| RAN26 | G | A | A | A | G | T | G | G | T | T | C | C | G | G | T | G | A | A | C |
| RAN27 | T | A | A | C | A | G | A | A | G | C | C | C | A | G | T | G | T | A | G |
| RAN28 | G | A | A | C | G | T | T | C | G | C | C | A | G | C | A | T | C | G | G |
| RAN29 | A | T | C | T | G | C | C | C | C | G | A | G | A | A | A | C | C | A | A |
| RAN30 | C | G | T | C | C | T | T | T | C | G | C | A | A | A | A | C | C | A | A |
| RAN31 | C | C | C | A | T | T | G | T | G | A | A | T | G | A | C | C | G | C | T |
| RAN32 | A | C | G | A | C | T | C | A | G | C | A | A | C | G | G | C | G | A | T |
| RAN33 | A | T | G | G | G | T | G | A | C | G | A | A | G | T | C | T | T | T | C |
| RAN34 | C | A | C | C | G | G | G | C | C | T | T | T | T | A | C | T | A | C | C |
| RAN35 | A | A | C | A | C | G | C | C | A | C | T | G | T | T | C | G | G | C | A |
| RAN36 | G | T | A | T | C | T | T | C | T | G | G | G | T | C | G | C | G | A | A |

FIG. 23

| FIG. 23A | FIG. 23B |
|---|---|

FIG. 23B

IF(AND(W23>40,W23<65,X23>55,X23<75,Y23>-4,Z23>-4AA23>
-6,AB23>0,AC23>-9),"YES,"NO")

| | | %GC | 0.6 pM<br>1 M NaCl<br>Tm (*C) | KCAL/MOL<br>3'-DIMER<br>(+) | KCAL/MOL<br>3'-DIMER<br>(-) | KCAL/MOL<br>DIMER<br>(+) | KCAL/MOL<br>HAIRPIN | 2 PENTAMERS<br>KCAL/MOL<br>3' END ΔG | ACCEPTABLE<br>OLIGO ? |
|---|---|---|---|---|---|---|---|---|---|
| G | C | 76.2 | 79.9 | -3.1 | -6.6 | -6.6 | -0.5 | -13.0 | NO |
| C | A | 23.8 | 50.6 | NONE | -2.5 | -3.6 | 1.1 | -7.0 | NO |
| A | G | 42.9 | 61.8 | NONE | NONE | -10.0 | -1.7 | -6.0 | NO |
| G | A | 33.3 | 54.7 | NONE | -1.3 | -4.8 | 1.2 | -6.0 | NO |
| C | C | 33.3 | 56.1 | NONE | NONE | -5.3 | 1.2 | -9.5 | NO |
| G | C | 33.3 | 61.0 | -3.1 | -3.5 | -3.6 | 1.7 | -9.5 | NO |
| G | T | 76.2 | 81.1 | NONE | -3.1 | -10.1 | NONE | -7.0 | NO |
| A | A | 23.8 | 55.6 | -4.8 | -1.9 | -5.3 | 0.3 | -6.5 | NO |
| T | T | 42.9 | 66.1 | -5.3 | -1.6 | -5.3 | NONE | -7.0 | NO |
| T | T | 42.9 | 64.5 | NONE | -1.0 | -3.6 | NONE | -7.0 | YES |
| A | C | 61.9 | 74.3 | NONE | -1.6 | -6.3 | -0.6 | -9.5 | NO |
| C | C | 47.6 | 60.0 | NONE | -1.9 | -8.8 | NONE | -9.5 | NO |
| C | G | 38.1 | 59.7 | -3.6 | -1.6 | -11.6 | 1.7 | -8.0 | NO |
| G | T | 57.1 | 71.0 | -1.3 | -1.9 | -10.1 | NONE | -7.5 | NO |
| G | A | 47.6 | 61.6 | -4.2 | -1.6 | -9.8 | 0.7 | -5.5 | NO |
| T | C | 52.4 | 66.2 | -1.6 | -1.6 | -3.6 | 1.1 | -6.5 | YES |
| C | G | 61.9 | 76.9 | -6.7 | -4.4 | -9.8 | -1.5 | -10.0 | NO |
| G | G | 52.4 | 64.6 | -4.7 | -1.9 | -4.7 | NONE | -7.0 | NO |
| A | A | 47.6 | 65.9 | -3.8 | NONE | -5.3 | NONE | -7.0 | YES |
| G | T | 33.3 | 58.5 | NONE | -3.1 | -9.8 | 1.3 | -6.5 | NO |
| T | A | 52.4 | 67.6 | -1.0 | -1.0 | -5.1 | 1.0 | -9.0 | NO |
| C | C | 66.7 | 79.1 | -9.3 | -6.3 | -10.3 | -2.2 | -11.0 | NO |
| T | C | 47.6 | 58.5 | -9.5 | -1.3 | -9.5 | 0.5 | -8.0 | NO |
| G | A | 42.9 | 57.5 | NONE | NONE | -4.2 | 1.9 | -6.5 | YES |
| G | A | 47.6 | 62.9 | -1.6 | -1.6 | -4.7 | NONE | -9.5 | NO |
| G | C | 57.1 | 71.0 | -3.1 | -3.5 | -9.8 | -0.3 | -10.0 | NO |
| G | A | 47.6 | 62.7 | NONE | -1.0 | -3.6 | 0.9 | -9.5 | NO |
| G | A | 57.1 | 73.0 | -1.6 | -13.2 | -13.5 | -0.6 | -8.0 | NO |
| C | A | 52.4 | 70.9 | -1.9 | -1.5 | -3.6 | 1.1 | -7.0 | YES |
| A | C | 42.9 | 66.4 | -1.3 | -3.6 | -5.7 | -1.1 | -6.5 | NO |
| G | G | 57.1 | 72.3 | -8.1 | -8.1 | -8.1 | -2.9 | -9.5 | NO |
| A | C | 57.1 | 69.4 | NONE | NONE | -3.6 | NONE | -5.5 | YES |
| T | G | 47.6 | 63.5 | -1.9 | -1.5 | -3.5 | NONE | -7.0 | YES |
| T | G | 57.1 | 70.9 | -1.9 | -1.9 | -9.8 | -2.1 | -9.5 | NO |
| G | G | 61.9 | 72.1 | -5.0 | NONE | -5.0 | -0.8 | -9.5 | NO |
| C | T | 52.4 | 65.4 | NONE | -1.3 | -13.5 | 0.6 | -6.5 | NO |

```
5'-gggAgCgAATgTTAgggCACACTCATgggTgAgCAAgTCTTTCTgTAAgggCTgATgTCAggCgTATTgACAAgCATgACgACCAgA-3'
3'-cccTCgCTTACAATCCCgTgTgAgTACCCACTCgTTCAgAAAgACATTCCCgACTACAgTCCgCATAACTgTTCgTACTgCTggTCT-5'

RAN16 PRIMER: 5'-AgCgAATgTTAgggCACACTC-3'                           5'-TAAgggCTgATgTCAggCgTA-3'   RAN21 AMVE-PROBE
TARGET:    5'-gggAgCgAATgTTAgggCACACTCATgggTgAgCAAgTCTTTCTgTAAgggCTgATgTCAggCgTATTgACAAgCATgACCAgA-3'
                                  RAN33 AKP-PROBE:   5'-ATgggTgAgCAAgTCTTTCTg-3'           3'-AACTgTTCgTACTggTCT AgAgggATATCACTCAgCATAATTTAA-5'
                                                                     (T7 PROMOTER / RAN19 PRIMER)
               (T3 PROMOTER)
5'-GCAATTAACCCTCACTAAAGGGAgCgAATgTTAgggCACACTCATgggTgAgCAAgTC-3'
3'-gTACCCACTCgTTCAgAAAgACATTCCCgACTACAgTCCgCATAACTgTTCgTACTgCTggTCT-5'

OLIGOS
RAN16 TMA PRIMER:       5'-AgC gAA TgT TAg ggC ACA CTC-3'
RAN21 AMVE-PROBE:       5'-AMINOLINK-TAA ggg CTg ATg TCA ggC gTA-3'
RAN33 AKP-PROBE:        5'-AMINOLINK-ATg ggT gAg CAA gTC TTT CTg-3'
T7/RAN19 TMA PRIMER:    5'-AAT TTA ATA CgA CTC ACT ATA ggg AgA TCT ggT CgT CAT gCT TgT CAA-3'
RIC1 DETECTION OLIGO:   5'-CAA TAC gCC TgA CAT CAC TAA AGG GAg CgA ATg TTA ggg CAC ACT CAT ggg TgA gCA AgT C-3'
RIC1 TOP OLIGO:         5'-GCA ATT AAC CCT CAC TAA AGG GAg CgA ATg TTA ggg CAC ACT CAT ggg TgA gCA AgT C-3'
RIC1 BOTTOM OLIGO:      5'-TCT ggT CgT CAT gCT TgT CAA TAC gCC TgA CAT CAC CCC TTA CAg AAA gAC TTg CTC ACC CAT g-3'
```

| AMPLIFICATION OF PURIFIED RIC1 RNA | | | | | | | | |
|---|---|---|---|---|---|---|---|---|
| POSITION | RIC1 RNA* | CT RNA | AKP TYPE & SPR TYPE | 0 MIN | 1.8 MIN | 5.4 MIN | 14.6 MIN | 40.0 MIN |
| C1 | NONE | NONE | RIC1 | 56 | 56 | 58 | 61 | 70 |
| C2 | " | NONE | RIC1 | 57 | 55 | 57 | 59 | 66 |
| C3 | 0.1 | NONE | RIC1 | 56 | 55 | 57 | 61 | 70 |
| C4 | " | NONE | RIC1 | 57 | 56 | 57 | 61 | 68 |
| C5 | 1 | NONE | RIC1 | 56 | 55 | 59 | 65 | 81 |
| C6 | " | NONE | RIC1 | 56 | 55 | 57 | 62 | 74 |
| D1 | 10 | NONE | RIC1 | 55 | 78 | 114 | 202 | 414 |
| D2 | " | NONE | RIC1 | 56 | 56 | 59 | 66 | 82 |
| D3 | 100 | NONE | RIC1 | 56 | 55 | 58 | 62 | 73 |
| D4 | " | NONE | RIC1 | 57 | 57 | 61 | 70 | 94 |
| D5 | 10000 | NONE | RIC1 | 56 | 58 | 81 | 119 | 227 |
| D6 | " | NONE | RIC1 | 56 | 57 | 70 | 102 | 184 |
| E1 | 100000 | NONE | RIC1 | 56 | 93 | 209 | 414 | 948 |
| E2 | " | NONE | RIC1 | 56 | 105 | 246 | 497 | 1155 |
| E3 | 1000000 | NONE | RIC1 | 56 | 395 | 1474 | 3029 | 6510 |
| E4 | " | NONE | RIC1 | 56 | 596 | 1981 | 4309 | 7830 |
| E5 | 10000000 | NONE | RIC1 | 56 | 985 | 3597 | 7371 | 10840 |
| E6 | " | NONE | RIC1 | 55 | 1062 | 3617 | 7464 | 10839 |

AMPLIFICATION PERFORMED WITH CT REAGENTS, SPIKED WITH RIC1 PRIMERS (25 pmol RAN 16 AND 5 pmol T7/RAN 19)
EACH SAMPLE IS AN INDEPENDENT AMPLIFICATION.
RIC1 SPRs COATED AT 0.5 ng/μl INSTEAD OF THE "NORMAL" 1.0 μg/μl LEVEL.

SEQUENCE LISTING

<160> NUMBER OF SEQ ID NOS: 51

<210> SEQ ID NO 1
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran1

<400> SEQUENCE: 1
gcaggtctgc tcccgagccg c                                          21

<210> SEQ ID NO 2
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran2

<400> SEQUENCE: 2
tattacgaca ttatacaatc a                                          21

<210> SEQ ID NO 3
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: ran3

<400> SEQUENCE: 3
gggacgttca aacgttataa g                                          21

<210> SEQ ID NO 4
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran4

```
<400> SEQUENCE: 4
acgctaacaa gtacattaag a                                              21

<210> SEQ ID NO 5
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran5

<400> SEQUENCE: 5
acttatacca tttaatgagc c                                              21

<210> SEQ ID NO 6
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran6

<400> SEQUENCE: 6
tataaatgac gcataaatgg c                                              21

<210> SEQ ID NO 7
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran7

<400> SEQUENCE: 7
cccccggcgc tgcaggtagg t                                              21

<210> SEQ ID NO 8
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran8

<400> SEQUENCE: 8
tgttgactaa accaaaatta a                                              21

<210> SEQ ID NO 9
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran9

<400> SEQUENCE: 9
tcggttgagc aggagaaaat t                                              21

<210> SEQ ID NO 10
<211> LENGTH: 21
<212> TYPE: DNA
<213> ORGANISM: Artificial Sequence
```

```
<220> FEATURE:
<223> OTHER INFORMATION: Randomly generated nucleic acid molecule
<221> NAME/KEY: misc_feature
<223> OTHER INFORMATION: Ran10

<400> SEQUENCE: 10
tactgatgga tgccgatgat t                                              21

<210> SEQ ID NO 11
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran11

<400> SEQUENCE: 11
ctgccgattt ggagctgcca c                                              21

<210> SEQ ID NO 12
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran12

<400> SEQUENCE: 12
aagttactag taccccaagc c                                              21

<210> SEQ ID NO 13
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran13

<400> SEQUENCE: 13
tccaatattg aacttcagtc g                                              21

<210> SEQ ID NO 14
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran14

<400> SEQUENCE: 14
caactttcgc ccagctgagg t                                              21

<210> SEQ ID NO 15
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran15

<400> SEQUENCE: 15
ctctacaatc agccggatag a                                              21
```

```
<210> SEQ ID NO 16
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran16

<400> SEQUENCE: 16
agcgaatgtt agggcacact c                                              21

<210> SEQ ID NO 17
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran17

<400> SEQUENCE: 17
accggcaaag gttgggttcc g                                              21

<210> SEQ ID NO 18
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran18

<400> SEQUENCE: 18
ttcacaacgc actcctctag g                                              21

<210> SEQ ID NO 19
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran19

<400> SEQUENCE: 19
tctggtcgtc atgcttgtca a                                              21

<210> SEQ ID NO 20
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran20

<400> SEQUENCE: 20
gattaaatat ccggtgaatg t                                              21

<210> SEQ ID NO 21
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran21
```

<400> SEQUENCE: 21
taagggctga tgtcaggcgt a                                             21

<210> SEQ ID NO 22
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran22

<400> SEQUENCE: 22
aaccgcgaac gggttcaggc c                                             21

<210> SEQ ID NO 23
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran23

<400> SEQUENCE: 23
gttactttct gctgtgagct c                                             21

<210> SEQ ID NO 24
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran24

<400> SEQUENCE: 24
actagaacgg aaccttagag a                                             21

<210> SEQ ID NO 25
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran25

<400> SEQUENCE: 25
gaggatctta caaacgaggg a                                             21

<210> SEQ ID NO 26
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran26

<400> SEQUENCE: 26
gaaagtggtt ccggtgaacg c                                             21

<210> SEQ ID NO 27
<211> LENGTH: 21
<212> TYPE: DNA

```
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran27

<400> SEQUENCE: 27
taacagaagc cagtgtacgg a                                              21

<210> SEQ ID NO 28
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran28

<400> SEQUENCE: 28
gaacgttcgc gacatcgtgg a                                              21

<210> SEQ ID NO 29
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran30

<400> SEQUENCE: 29
atctgccccg agaaaccaac a                                              21

<210> SEQ ID NO 30
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran30

<400> SEQUENCE: 30
cgtccttttc aaaccgaaa c                                               21

<210> SEQ ID NO 31
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran31

<400> SEQUENCE: 31
cccattgtga atgacgctgg g                                              21

<210> SEQ ID NO 32
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran32

<400> SEQUENCE: 32
acgactcagc acggcgaata c                                              21
```

<210> SEQ ID NO 33
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran33

<400> SEQUENCE: 33
atgggtgagc aagtctttct g                                          21

<210> SEQ ID NO 34
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran34

<400> SEQUENCE: 34
caccgggcct tttatagcct g                                          21

<210> SEQ ID NO 35
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran35

<400> SEQUENCE: 35
aacacgccac tgtcctgctg g                                          21

<210> SEQ ID NO 36
<211> LENGTH: 21
<212> TYPE: DNA
<213> ORGANISM: Artificial Sequence
<220> FEATURE:
<223> OTHER INFORMATION: Randomly generated nucleic acid molecule
<221> NAME/KEY: misc_feature
<223> OTHER INFORMATION: Ran36

<400> SEQUENCE: 36
gtatcttctg ggtcgcgaac t                                          21

<210> SEQ ID NO 37
<211> LENGTH: 87
<212> TYPE: DNA
<213> ORGANISM: Artificial Sequence
<220> FEATURE:
<223> OTHER INFORMATION: Random internal control sequence
<221> NAME/KEY: misc_feature
<223> OTHER INFORMATION: RIC1

<400> SEQUENCE: 37
gggagcgaat gttagggcac actcatgggt gagcaagtct ttctgtaagg gctgatgtca    60
ggcgtattga caagcatgac gaccaga                                       87

<210> SEQ ID NO 38
<211> LENGTH: 48
<212> TYPE: DNA
<213> ORGANISM: Artificial Sequence
<220> FEATURE:

```
<223> OTHER INFORMATION: T7 promoter/ RAN19 primer
<221> NAME/KEY: misc_feature
<223> OTHER INFORMATION: T7 promoter/RAN19 Primer

<400> SEQUENCE: 38
aatttaatac gactcactat agggagatct ggtcgtcatg cttgtcaa            48

<210> SEQ ID NO 39
<211> LENGTH: 56
<212> TYPE: DNA
<213> ORGANISM: Artificial Sequence
<220> FEATURE:
<223> OTHER INFORMATION: RIC1 top oligonucleotide
<221> NAME/KEY: misc_feature
<223> OTHER INFORMATION: RIC1 top oligonucleotide

<400> SEQUENCE: 39
gcaattaacc ctcactaaag ggagcgaatg ttagggcaca tcatgggtga gcagtc    56

<210> SEQ ID NO 40
<211> LENGTH: 64
<212> TYPE: DNA
<213> ORGANISM: Artificial Sequence
<220> FEATURE:
<223> OTHER INFORMATION: RIC1 bottom oligonucleotide
<221> NAME/KEY: misc_feature
<223> OTHER INFORMATION: RIC1 bottom oligonucleotide

<400> SEQUENCE: 40
tctggtcgtc atgcttgtca atacgcctga catcagccct tacagaaaga cttgctcacc   60
catg                                                               64

<210> SEQ ID NO 41
<211> LENGTH: 22
<212> TYPE: DNA
<213> ORGANISM: Artificial Sequence
<220> FEATURE:
<223> OTHER INFORMATION: RAN21 AMVE-probe
<221> NAME/KEY: misc_feature
<223> OTHER INFORMATION: Ran21 AMVE-Probe
<221> NAME/KEY: misc_feature
<222> LOCATION: (1)..(1)
<223> OTHER INFORMATION: N stands for aminolink

<400> SEQUENCE: 41
ntaagggctg atgtcaggcg ta                                         22

<210> SEQ ID NO 42
<211> LENGTH: 22
<212> TYPE: DNA
<213> ORGANISM: Artificial Sequence
<220> FEATURE:
<223> OTHER INFORMATION: RAN33 AKP-probe
<221> NAME/KEY: misc_feature
<223> OTHER INFORMATION: Ran 33 AKP-Probe
<221> NAME/KEY: misc_feature
<222> LOCATION: (1)..(1)
<223> OTHER INFORMATION: N stands for aminolink

<400> SEQUENCE: 42
natgggtgag caagtctttc tg                                         22

<210> SEQ ID NO 43
<211> LENGTH: 48
<212> TYPE: DNA
<213> ORGANISM: Artificial Sequence
<220> FEATURE:
<223> OTHER INFORMATION: RIC1 detection probe
```

```
<221> NAME/KEY: misc_feature
<223> OTHER INFORMATION: RIC1 Detection oligonucleotide

<400> SEQUENCE: 43
caatacgcct gacatcagcc cttacagaaa gacttgctca cccatgag              48

<210> SEQ ID NO 44
<211> LENGTH: 96
<212> TYPE: DNA
<213> ORGANISM: Artificial Sequence
<220> FEATURE:
<223> OTHER INFORMATION: Random internal control sequence
<221> NAME/KEY: misc_feature
<223> OTHER INFORMATION: RIC2

<400> SEQUENCE: 44
cagtagaggt agggctgct aggagtataa cagaagccag tgtacggaac gactcagcac    60
ggcgaatact ttgctaccag acctagagga gtgcgt                             96

<210> SEQ ID NO 45
<211> LENGTH: 26
<212> TYPE: DNA
<213> ORGANISM: Artificial Sequence
<220> FEATURE:
<223> OTHER INFORMATION: RAN51 TMA primer
<221> NAME/KEY: misc_feature
<223> OTHER INFORMATION: RAN51 TMA Primer

<400> SEQUENCE: 45
cagtagaggt agggctgct aggagt                                         26

<210> SEQ ID NO 46
<211> LENGTH: 52
<212> TYPE: DNA
<213> ORGANISM: Artificial Sequence
<220> FEATURE:
<223> OTHER INFORMATION: T7 promoter/RAN39 primer
<221> NAME/KEY: misc_feature
<223> OTHER INFORMATION: T7 promoter/RAN39 Primer

<400> SEQUENCE: 46
aatttaatac gactcactat agggagaacg cactcctcta ggtctggtag ca           52

<210> SEQ ID NO 47
<211> LENGTH: 67
<212> TYPE: DNA
<213> ORGANISM: Artificial Sequence
<220> FEATURE:
<223> OTHER INFORMATION: RIC2 top oligonucleotide
<221> NAME/KEY: misc_feature
<223> OTHER INFORMATION: RIC2 top oligonucleotide

<400> SEQUENCE: 47
gcaattaacc ctcactaaag ggcagtagag gtagggctg ctaggagtat aacagaagcc    60
agtgtac                                                             67

<210> SEQ ID NO 48
<211> LENGTH: 66
<212> TYPE: DNA
<213> ORGANISM: Artificial Sequence
<220> FEATURE:
<223> OTHER INFORMATION: RIC2 bottom oligonucleotide
<221> NAME/KEY: misc_feature
<223> OTHER INFORMATION: RIC2 bottom oligonucleotide

<400> SEQUENCE: 48
```

```
acgcactcct ctaggtctgg tagcaaagta ttcgccgtgc tgagtcgttc cgtacactgg         60
cttctg                                                                    66

<210> SEQ ID NO 49
<211> LENGTH: 22
<212> TYPE: DNA
<213> ORGANISM: Artificial Sequence
<220> FEATURE:
<223> OTHER INFORMATION: RAN27 AMVE-probe
<221> NAME/KEY: misc_feature
<223> OTHER INFORMATION: RAN27 AMVE-Probe
<221> NAME/KEY: misc_feature
<222> LOCATION: (1)..(1)
<223> OTHER INFORMATION: N stands for aminolink

<400> SEQUENCE: 49
ntaacagaag ccagtgtacg ga                                                  22

<210> SEQ ID NO 50
<211> LENGTH: 22
<212> TYPE: DNA
<213> ORGANISM: Artificial Sequence
<220> FEATURE:
<223> OTHER INFORMATION: RAN32 AKP-probe
<221> NAME/KEY: misc_feature
<223> OTHER INFORMATION: RAN32 AKP-Probe
<221> NAME/KEY: misc_feature
<222> LOCATION: (1)..(1)
<223> OTHER INFORMATION: N stands for aminolink

<400> SEQUENCE: 50
nacgactcag cacggcgaat ac                                                  22

<210> SEQ ID NO 51
<211> LENGTH: 47
<212> TYPE: DNA
<213> ORGANISM: Artificial Sequence
<220> FEATURE:
<223> OTHER INFORMATION: RIC2 detection oligonucleotide
<221> NAME/KEY: misc_feature
<223> OTHER INFORMATION: RIC2 Detection oligonucleotide

<400> SEQUENCE: 51
aagtattcgc cgtgctgagt cgttccgtac actggcttct gttatac                       47
```

NUCLEIC ACID ASSAYS

This application is a continuation of Ser. No. 08/850,171 May 2, 1997, abandoned.

FIELD OF THE INVENTION

The present invention relates to the detection of specific nucleic acid sequences in a target test sample.

In particular, the present invention relates to the automated detection of specific nucleic acid sequences which are either unamplified or amplified nucleic acid sequences (amplicons).

In addition, the present invention relates to the use of automated amplification, methods and compositions for monitoring successful amplification, improved methods for reducing the chance for contamination, and the use of unified reaction buffers and unit dose aliquots of reaction components for amplification.

Finally, the present invention also relates to unique constructs and methods for the conventional or automated detection of one, or more than one different nucleic acid sequences in a single assay.

THE BACKGROUND OF THE INVENTION

The development of techniques for the manipulation of nucleic acids, the amplification of such nucleic acids when necessary, and the subsequent detection of specific sequences of nucleic acids or amplicons has generated extremely sensitive and nucleic acid sequence specific assays for the diagnosis of disease and/or identification of pathogenic organisms in a test sample.

Amplification of Nucleic Acids

When necessary, enzymatic amplification of nucleic acid sequences will enhance the ability to detect such nucleic acid sequences. Generally, the currently known amplification schemes can be broadly grouped into two classes based on whether, the enzymatic amplification reactions are driven by continuous cycling of the temperature between the denaturation temperature, the primer annealing temperature, and the amplicon (product of enzymatic amplification of nucleic acid) synthesis temperature, or whether the temperature is kept constant throughout the enzymatic amplification process (isothermal amplification). Typical cycling nucleic acid amplification technologies (thermocycling) are polymerase chain reaction (PCR), and ligase chain reaction (LCR). Specific protocols for such reactions are discussed in, for example, *Short Protocols in Molecular Biology 2<sup>nd</sup> Edition, A Compendium of Methods from Current Protocols in Molecular Biology*, (Eds. Ausubel et al., John Wiley & Sons, New York, 1992) chapter 15. Reactions which are isothermal include: transcription-mediated amplification (TMA), nucleic acid sequence-based amplification (NASBA), and strand displacement amplification (SDA).

U.S. Patent documents which discuss nucleic acid amplification include U.S. Pat. No. 4,683,195; 4,683,202; 5,130,238; 4,876,187; 5,030,557; 5,399,491; 5,409,818; 5,485,184; 5,409,818; 5,554,517; 5,437,990 and 5,554,516 (each of which are hereby incorporated by reference in their entirety). It is well known that methods such as those described in these patents permit the amplification and detection of nucleic acids without requiring cloning, and are responsible for the most sensitive assays for nucleic acid sequences. However, it is equally well recognized that along with the sensitivity of detection possible with nucleic acid amplification, the ease of contamination by minute amounts of unwanted exogenous nucleic acid sequences is extremely great. Contamination by unwanted exogenous DNA or RNA nucleic acids is equally likely. The utility of amplification reactions will be enhanced by methods to control the introduction of unwanted exogenous nucleic acids and other contaminants.

Prior to the discovery of thermostable enzymes, methods that used thermocycling were made extremely difficult by the requirement for the addition of fresh enzyme after each denaturation step, since initially the elevated temperatures required for denaturation also inactivated the polymerases. Once thermostable enzymes were discovered, cycling nucleic acid amplification became a far more simplified procedure where the addition of enzyme was only needed at the beginning of the reaction. Thus reaction tubes did not need to be opened and new enzyme did not need to be added during the reaction, allowed for an improvement in efficiency and accuracy as the risk of contamination was reduced, and the cost of enzymes was also reduced. An example of a thermostable enzyme is the polymerase isolated from the organism *Thermophilus aquaticus*.

In general, isothermal amplification can require the combined activity of multiple enzyme activities for which no optimal thermostable variants have been described. The initial step of an amplification reaction will usually require denaturation of the nucleic acid target, for example in the TMA reaction, the initial denaturation step is usually $\geq 65°$ C., but can be typically $\geq 95°$ C., and is used when required to remove the secondary structure of the target nucleic acid.

The reaction mixture is then cooled to a lower temperature which allows for primer annealing, and is the optimal reaction temperature for the combined activities of the amplification enzymes. For example, in TMA the enzymes are generally a T7 RNA polymerase and a reverse transcriptase (which includes endogenous RNase H activity). The temperature of the reaction is kept constant through out the subsequent isothermal amplification cycle.

Because of the lack of suitable thermostable enzymes, some isothermal amplifications will generally require the addition of enzymes to the reaction mixture after denaturation at high temperature, and cool-down to a lower temperature. This requirement is inconvenient, and requires the opening of the amplification reaction tube, which introduces a major opportunity for contamination.

Thus, it would be most useful if such reactions could be more easily performed with a reduced risk of contamination by methods which would allow for integrated denaturation and amplification without the need for manual enzyme transfer.

Amplification Buffer and Single Reaction Aliquot of Reagents

Typical reaction protocols require the use of several different buffers, tailored to optimize the activity of the particular enzyme being used at certain steps in the reaction, or for optimal resuspension of reaction components. For example, while a typical PCR 10× amplification buffer will contain 500 mM KCl and 100 mM Tris HCl, pH 8.4, the concentration of $MgCl_2$ will depend upon the nucleic acid target sequence and primer set of interest. Reverse transcription buffer (5×) typically contains 400 mM Tris-Cl, pH 8.2; 400 mM KCl and 300 mM $MgCl_2$, whereas Murine Maloney Leukemia Virus reverse transcriptase buffer (5×) typically contains 250 mM Tris-Cl, pH 8.3; 375 mM KCl; 50 mM DTT (Dithiothreitol) and 15 mM $MgCl_2$.

While such reaction buffers can be prepared in bulk from stock chemicals, most commercially available amplification products provide bulk packaged reagents and specific buffers for use with the amplification protocol. For example, commercially available manual amplification assays for detection of clinically significant pathogens (for example Gen-Probe Inc. Chlamydia, and *Mycobacterium tuberculosis* detection assays) requires several manual manipulations to perform the assay, including dilution of the test sample in a sample dilution buffer (SDB), combination of the diluted sample with amplification reaction reagents such as oligonucleotides and specific oligonucleotide promoter/primers which have been reconstituted in an amplification reconstitution buffer (ARB), and finally, the addition to this reaction mixture of enzymes reconstituted in an enzyme dilution buffer (EDB).

The preparation and use of multiple buffers which requires multiple manual additions to the reaction mixture introduces a greater chance for contamination. It would be most useful to have a single unified buffer which could be used in all phases of an amplification protocol. In particular, with the commercially available TMA assays described above, the requirement for three buffers greatly complicates automation of such a protocol.

Bulk packaging of the enzyme or other reaction components by manufacturers, may require reconstitution of the components in large quantities, and the use of stock amounts of multiple reagents, can be wasteful when less than the maximal number of reactions are to be carried out, as some of these components may be stable for only a short time. This process of reconstitution also requires multiple manipulations by the user of the stock reagents, and aliquoting of individual reaction amounts of reagents from stocks which creates a major opportunity for contamination.

Methods and compositions for the preparation of bulk quantities of preserved proteins are known, see for example, U.S. Pat. No. 5,098,893; 4,762,857; 4,457,916; 4,891,319; 5,026,566 and International Patent Publications WO 89/06542; WO 93/00806; WO 95/33488 and WO 89/00012, all of which are hereby incorporated by reference in their entirety. However, the use of pre-aliquoted and preserved reagent components in single reaction quantities/dose is both very useful and economical. Single aliquots of enzyme reagent avoids multiple use of bulk reagents, reducing waste, and greatly reducing the chance of contamination. Further, such single reaction aliquots are most suitable for the automation of the reaction process.

The requirement for many changes of buffer and the multiple addition of reagents complicates the automation of such reactions. A single dose unit of reaction buffer mixture, and a unified combination buffer will both simplify automation of the process and reduce the chance of contamination.

Automation of Nucleic Acid Detection with or without Amplification

Nucleic acid probe assays, and combination amplification/probe assays can be rapid, sensitive, highly specific, and usually require precise handling in order to minimize contamination with non-specific nucleic acids, and are thus prime candidates for automation. As with conventional nucleic acid detection protocols, it is generally required to utilize a detection probe oligonucleotide sequence which is linked by some means to a detectable signal generating component. One possible probe detection system is described in U.S. Pat. No. 4,581,333 hereby incorporated by reference in its entirety.

In addition, automation of a nucleic acid detection system targeting unamplified or amplified nucleic acid, or a combined automated amplification/detection system will generally be adaptable to the use of nucleic acid capture oligonucleotides that are attached to some form of solid support system. Examples of such attachment and methods for attachment of nucleic acid to solid support are found in U.S. Pat. Nos. 5,489,653 and 5,510,084 both of which are hereby incorporated by reference.

Automation of amplification, detection, and a combination of amplification and detection is desirable to reduce the requirement of multiple user interactions with the assay. Apparatus and methods for optically analyzing test materials are described for example in U.S. Pat. No. 5,122,284 (hereby incorporated by reference in its entirety). Automation is generally believed to be more economical, efficient, reproducible and accurate for the processing of clinical assays. Thus with the superior sensitivity and specificity of nucleic acid detection assays, the use of amplification of nucleic acid sequences, and automation at one or more phases of a assay protocol can enhance the utility of the assay protocol and its utility in a clinical setting.

Advantage of Internal Control Sequences

Nucleic acid amplification is highly sensitive to reaction conditions, and the failure to amplify and/or detect any specific nucleic acid sequences in a sample may be due to error in the amplification process as much as being due to absence of desired target sequence. Amplification reactions are notoriously sensitive to reaction conditions and have generally required including control reactions with known nucleic acid target and primers in separate reaction vessels treated at the same time. However, internal control sequences added into the test reaction mixture would truly control for the success of the amplification process in the subject test reaction mixture and would be most useful. U.S. Pat. No. 5,457,027 (hereby incorporated by reference in its entirety) teaches certain internal control sequences which are useful as an internal oligonucleotide standard in isothermal amplification reactions for *Mycobacterium tuberculosis*.

However it would be extremely useful to have a general method of generating internal control sequences, that would be useful as internal controls of the various amplification procedures, which are specifically tailored to be unaffected by the nucleic acid sequences present in the target organism, the host organism, or nucleic acids present in the normal flora or in the environment. Generally, such internal control sequences should not be substantially similar to any nucleic acid sequences present in a clinical setting including human, pathogenic organism, normal flora organisms, or environmental organisms which could interfere with the amplification and detection of the internal control sequences.

Detection of More than one Nucleic Acid Sequence in a Single Assay

In general, a single assay reaction for the detection of nucleic acid sequences is limited to the detection of a single target nucleic acid sequence. This single target limitation increases costs and time required to perform clinical diagnostic assays and verification control reactions. The detection of more than one nucleic acid sequence in a sample using a single assay would greatly enhance the efficiency of sample analysis and would be of a great economic benefit by reducing costs, for example helping to reduce the need for multiple clinical assays.

Multiple analyte detection in a single assay has been applied to antibody detection of analyte as in for example International Patent Publication number WO 89/00290 and WO 93/21346 both of which are hereby incorporated by reference in their entirety.

In addition to reducing cost, time required, the detection of more than one nucleic acid target sequence in a single assay would reduce the chance of erroneous results. In particular multiple detection would greatly enhance the utility and benefit using internal control sequences and allow for the rapid validation of negative results.

SUMMARY OF THE INVENTION

The present invention comprises methods for the automated isothermal amplification and detection of a specific nucleic acid in a test sample to be tested comprising:

a) combining a test sample to be tested with a buffer, a mixture of free nucleotides, specific oligonucleotide primers, and optionally thermostable nucleic acid polymerization enzyme, in a first reaction vessel and placing the reaction vessel in an automated apparatus such that;

b) the automated apparatus heats the first reaction vessel to a temperature, and for a time sufficient to denature, if necessary, the nucleic acid in the sample to be tested;

c) the automated apparatus cools the first reaction vessel to a temperature such that oligonucleotide primers can specifically anneal to the target nucleic acid;

d) the automated apparatus transfers the reaction mixture from the first reaction vessel to a second reaction vessel, and brings the reaction mixture in contact with thermolabile nucleic acid amplification enzyme;

e) the automated apparatus maintains the temperature of the second reaction vessel at a temperature which allows primer mediated amplification of the nucleic acid;

f) the automated apparatus contacts the amplified nucleic acid in the second reaction vessel with a capture nucleic acid specific for the nucleic acid to be tested such that they form a specifically-bound nucleic acid-capture probe complex;

g) the automated apparatus optionally washes the specifically captured amplified nucleic acid such that non-specifically bound nucleic acid is washed away from the specifically-bound nucleic acid-capture probe complex;

h) the automated apparatus contacts the specifically-bound nucleic acid-capture probe complex with a labeled nucleic acid probe specific for the amplified nucleic acid such that a complex is formed between the specifically amplified nucleic acid and the labeled nucleic acid probe;

i) the automated apparatus washes the specifically-bound nucleic acid-capture probe-labeled probe complex such that non-specifically bound labeled probe nucleic acid is washed away from the specifically bound complex;

j) the automated apparatus contacts the specifically bound complex with a solution wherein an detection reaction between the labeled nucleic acid probe is effected between the solution and the label attached to the nucleic acid such that a detectable signal is generated from the sample in proportion the amount of specifically-bound amplified nucleic acid in the sample;

wherein the steps h, i, and j may occur sequentially or simultaneously;

k) the automated apparatus detects the signal and optionally displays a value for the signal, or optionally records a value for the signal.

As used herein, the term test sample includes samples taken from living patients, from non-living patients, from surfaces, gas, vacuum or liquids, from tissues, bodily fluids, swabs from body surfaces or cavities, and any similar source. The term buffer as used here encompasses suitable formulations of buffer which can support the effective activity of a label, for example an enzyme placed into such buffer when treated at the appropriate temperature for activity and given the proper enzymatic substrate and templates as needed. The term specific oligonucleotide nucleic acid primers means an oligonucleotide having a nucleic acid sequence which is substantially complementary to and will specifically hybridize/anneal to a target nucleic acid of interest and may optionally contain a promoter sequence recognized by RNA polymerase. The term reaction vessel means a container in which a chemical reaction can be performed and preferably capable of withstanding temperatures of anywhere from about −80° C. to 100° C.

The instant invention further provides for the method described above, wherein the reaction buffer is a unified buffer and as such is suitable for denaturation nucleic acids and annealing of nucleic acids, and is further capable of sustaining the enzymatic activity of nucleic acid polymerization and amplification enzyme. Further encompassed by the invention is the method wherein the nucleic acid amplification enzyme is administered in the second reaction chamber as a single assay dose amount in a lyophilized pellet, and the reaction chamber is sealed prior to the amplification step.

The invention teaches an apparatus for the automated detection of more than one nucleic acid target sequences or amplicons comprising a solid phase receptacle (SPR® pipet-like devise) coated with at least two distinct zones of a capture nucleic acid oligonucleotide.

The invention teaches a method for the automated detection of more than one nucleic acid target sequence comprising contacting a solid phase receptacle (SPR® pipet-like devise) coated with at least two distinct capture nucleic acid oligonucleotides in a single or multiple zones to a sample to be tested and detecting a signal(s) from specifically bound probe. In one embodiment of the invention, the SPR® is coated with two distinct zones of capture nucleic acid oligonucleotides which are specific for different nucleic acid sequence targets. In another embodiment of the invention, the SPRY is coated with at least one capture probe for a target nucleic acid sequence, and one capture probe for an amplification control nucleic acid sequence which when detected confirms that amplification did take place.

The present invention also comprises an internal amplification positive control nucleic acid having the nucleic acid sequence of RIC1 and a second internal amplification positive control nucleic acid having the nucleic acid sequence of RIC2.

The present invention further comprises a method for generating an internal amplification positive control nucleic acid consisting of:

generating random nucleic acid sequences of at least 10 nucleotides in length, screening said random nucleic acid sequence and selecting for specific functionality, combining in tandem a number of such functionally selected nucleic acid sequences, and screening the combined nucleic acid sequence and optionally selecting against formation of intra-strand nucleic acid dimers, or the formation of hairpin structures.

BRIEF DESCRIPTION OF THE DRAWINGS

Presently preferred embodiments of the invention will be described in conjunction with the appended drawings, wherein like reference numerals refer to like elements in the various views, and in which:

FIG. 23 illustrates the results generated by the method described showing a collection of strings of nucleic acid sequences and screening for specific functional parameters. The SEQ ID NOs for the sequences are as follows: Ran1: SEQ ID NO:1; Ran2: SEQ ID NO:2; Ran3: SEQ ID NO:3; Ran4: SEQ ID NO:4; Ran5: SEQ ID NO:5; Ran6: SEQ ID NO:6; Ran7: SEQ ID NO:7; Ran8: SEQ ID NO:8; Ran9: SEQ ID NO:9; Ran10: SEQ ID NO:10; Ran11: SEQ ID NO:11; Ran12: SEQ ID NO:12; Ran13: SEQ ID NO:13; Ran14: SEQ ID NO:14; Ran15: SEQ ID NO:15; Ran16: SEQ ID NO:16; Ran17: SEQ ID NO:17; Ran18: SEQ ID NO:18; Ran19: SEQ ID NO:19; Ran20: SEQ ID NO:20; Ran21: SEQ ID NO:21; Ran22: SEQ ID NO:22; Ran23: SEQ ID NO:23; Ran24: SEQ ID NO:24; Ran25: SEQ ID NO:25; Ran26: SEQ ID NO:26; Ran27: SEQ ID NO:27; Ran28: SEQ ID NO:28; Ran29: SEQ ID NO:29; Ran30: SEQ ID NO:30; Ran31: SEQ ID NO:31; Ran32: SEQ ID NO:32; Ran33: SEQ ID NO:33; Ran34: SEQ ID NO:34; Ran35: SEQ ID NO:35; and Ran36: SEQ ID NO:36.

FIG. 24 shows the nucleic acid sequence of Random Internal Control 1 (RIC1) with the possible oligonucleotide primers/probes for amplification and detection of the control sequence.

FIG. 29 shows that RIC1 RNA, amplified by TMA and the chemically activated signal detected on a VIDAS instrument (bioMérieux Vitek, Inc.) using the enzyme-linked detection system, has a limit of sensitivity of about 1000 molecules of RIC1 RNA (without optimization of conditions).

DESCRIPTION OF THE INVENTION

Figure 1:
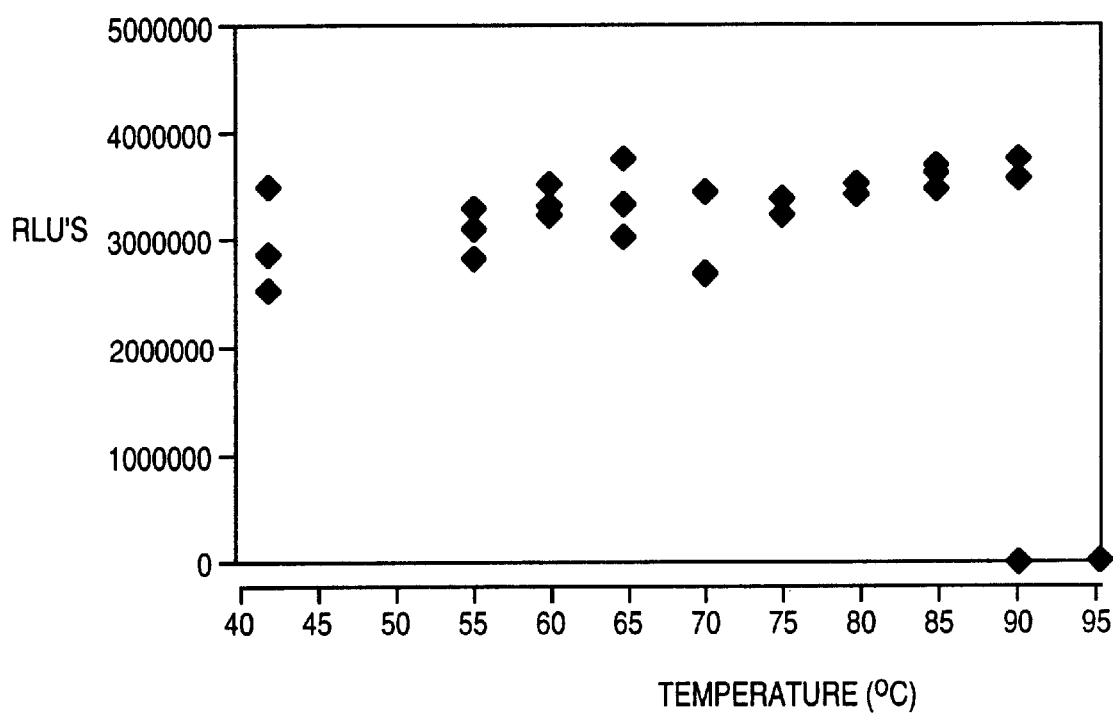
FIG. 1 is a graph illustrating single dose reagent pellet temperature stability.
Figure 2:
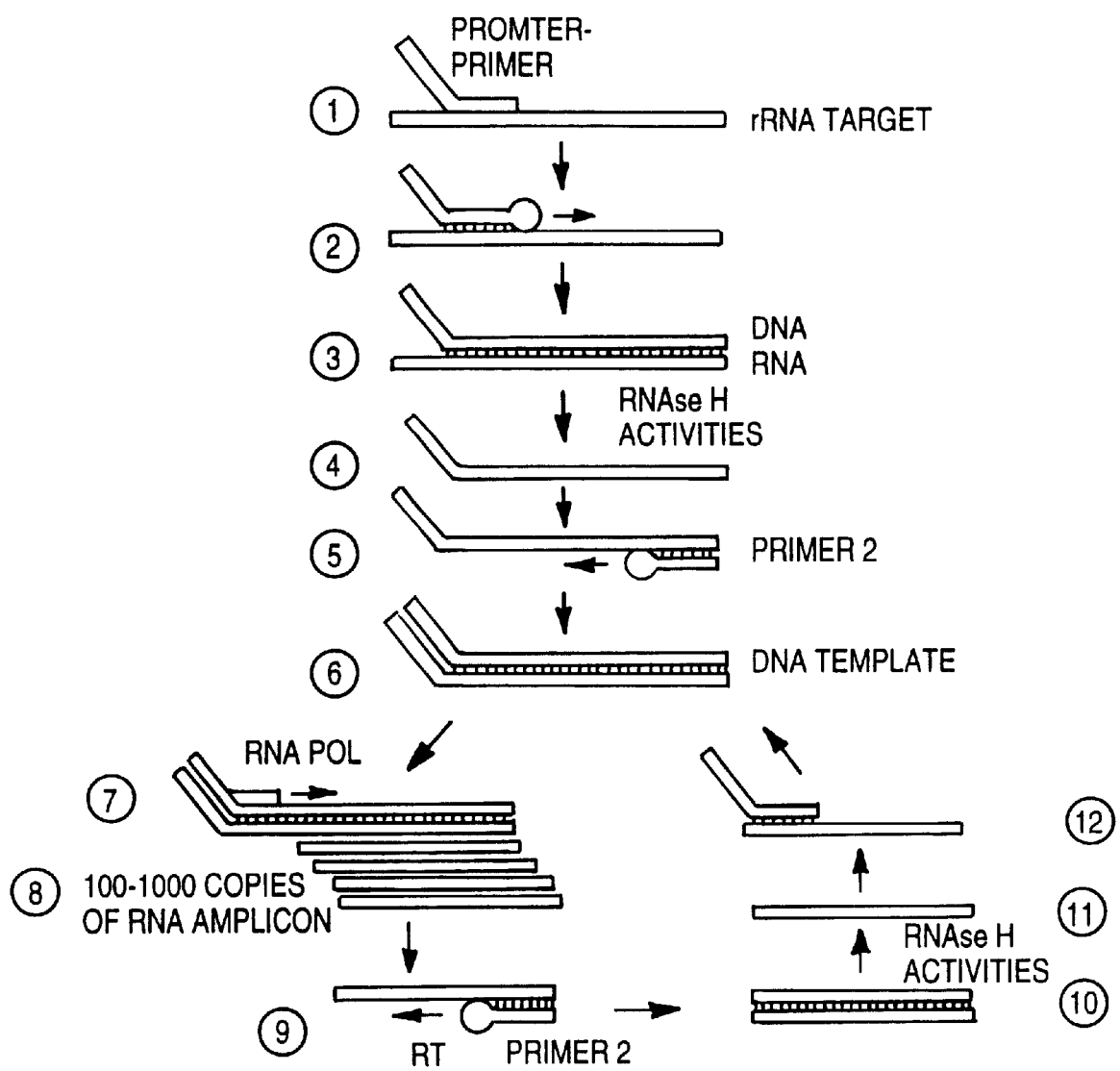
FIG. 2 illustrates the general TMA protocol.

The following examples are provided to better illustrate certain embodiments of the present invention without intending to limit the scope of the invention.

EXAMPLE 1

Single Dose Reagents and Unified Buffer

The implementation of a TMA reaction (see U.S. Pat. No. 5,437,990) on-line in a VIDAS or off-line in a separate instrument (with detection occurring on a VIDAS instrument) requires modification of the chemistry used to perform the reaction manually. First, bulk packaged reagents must be modified into single aliquot doses, and second, the buffer components of the reaction has been altered to form a single comprehensive multifunctional unified buffer solution.

Under the current manual technology, the reagents are prepared as lyophilized "cakes" of multiple-assay quantities. The amplification and enzyme reagents thus must be reconstituted in bulk and aliquoted for individual assays.

Thus the automated form of TMA on the VIDAS system improves on the above manual method by utilizing single dose pellets of lyophilized reaction components that can be resuspended in a single unified buffer which will support sample dilution, denaturation of nucleic acids, annealing of nucleic acids, and desired enzymatic activity.

A) Unified Buffer and Single Dose Reagents

To test the feasibility of single dose amplification reagents, standard Chlamydia TMA Amplification and Enzyme reagents (Gen-Probe Inc.), the bulk reagents were reconstituted in 0.75 ml of water. 12.5 µl of either the water reconstituted amplification or enzyme reagent (i.e. a single dose aliquots) were aliquoted into microcentrifuge tubes. These tubes were placed in a vacuum centrifuge with low heat to remove water. The end result of this procedure was microcentrifuge tube containing a small, dry cake of either enzyme or amplification reagent at the bottom of the tube.

The combined Unified Buffer used in this example, consists of a combination of standard commercially available Gen-Probe Inc. Sample Dilution Buffer (SDB), Amplification Reconstitution Buffer (ARB), and Enzyme Dilution Buffer (EDB) in a 2:1:1 ratio. To each dried amplification reagent microfuge tube was added 100 µl of the combined Unified Buffer, and positive control nucleic acid (+), and overlaid with 100 µl of silicone oil. The tube was then heated to 95° C. for 10 minutes and then cooled to 42° C. for 5 minutes. The 200 µl total volume was then transferred to a tube containing the dried enzyme reagent. This was then gently mixed to resuspend the enzyme reagent, and the solution was heated for one hour at 42° C.

Control reactions were prepared using Gen-Probe Control reagents which were reconstituted in the normal 1.5 ml of ARB or EDB according to instructions provided in the Gen-Probe kit. In each control reaction 25 µl of the reconstituted amplification reagent was combined with 50 µl or the SDB with the positive control nucleic acid (+). The mixture was also heated to 95° C. for 10 minutes and then cooled to 42° C. for 5 minutes. To this was added 25 µl of the reconstituted enzyme reagent and incubated at 42° C. for one hour. Negative control had no nucleic acid.

Both the test Unified Buffer (Unified) reactions and the standard Control (Control) reactions were then subjected to the Gen-Probe Inc. standard Hybridization Protection Assay (HPA) protocol. Briefly, 100 µl of a Chlamydia trachomatis specific nucleic acid probe was added to each tube and allowed to hybridize for 15 minutes at 60° C. Then 300 µl of Selection Reagent was added to each tube and the differential hydrolysis of hybridized and unhybridized probe was allowed to occur for 10 minutes. The tubes were then read in a Gen-Probe Inc. Leader 50 luninometer and the resultant data recorded as Relative Light Units (RLU) detected from the label, as shown in Table 1 below. Data reported as RLU, standard C. Trachomatis TMA/HPA reaction.

TABLE 1

Unified single dose aliquot of amplification and enzyme reagents

| Control (+) | Unified (+) | Control (−) | Unified (−) |
| --- | --- | --- | --- |
| 2,264,426 | 2,245,495 | 6,734 | 3,993 |
| 2,156,498 | 2,062,483 | 3,484 | 3,765 |
| 1,958,742 | 2,418,531 | 5,439 | 5,836 |
| 2,451,872 | 2,286,773 | | |
| 2,346,131 | 1,834,198 | | |

The data in Table 1 demonstrates that comparable results are obtained when using the single dose aliquots of dried amplification and enzyme reagent. In addition, the data shows that the results were comparable using three separate buffers (ARB, EDB and SDB) and one unified combined buffer (SDB, ARB and EDB combined at a ratio of 2:1:1) to resuspend the reagents and run the reactions.

B) Pellitization of Single Dose Reagents

In order to simplify the single dose aliquoting of reagents, methods which will allow for pelletization of these reagents in single dose aliquots were used. Briefly, reagent pellets (or beads) can be made by aliquoting an aqueous solution of the reagent of choice (that has been combined with an appropriate excipient, such as D(+) Trehalose (α-D-Glucopyranosyl-α-D-glucopyranoside, purchased from Pfanstiehl Laboratories, Inc., Waukegan, Ill.) into a cryogenic fluid, and then using sublimation to remove the water from the pellet. Once the reagent/trehalose mixture is aliquoted into the cryogenic fluid, it forms a spherical frozen pellet. These pellets are then placed in a lyophilizer where the frozen water molecules sublimate during the vacuum cycle. The result of this procedure is small, stable, non-flaking reagent pellets which can be dispensed into the appropriate packaging. Single dose aliquot pellets of reagents which contained RT, T7 and sugar were subjected to a wide range of temperatures to examine pellet stability. After being subject to a test temperature for 10 minutes, the pellets were then used for CT amplification. The results are graphed in FIG. 1. The results show that the single dose reagent pellet remains stable even after to exposure to high temperatures for 10 minutes.

The extraordinary stability of enzymes dried in trehalose has been previously reported (Colaco et al., 1992, Bio/Technology, 10, 1007) which has renewed interest in research on long-term stabilization of proteins has become a topic of interest (Franks, 1994, Bio/Technology, 12, 253). The resulting pellets of the amplification reagent and enzyme reagents were tested by use in C. Trachomatis TMA/HPA reactions.

The prepared amplification pellets were placed in a tube to which was added 75 µl of a mixture of ARB and SDB (mixed in a 1:2 ratio) with positive control nucleic acid. This sample was then heated to 95° C. for 10 minutes and then cooled to 42° C. for 5 minutes. To this was added 25 µl of enzyme reagent, which had been reconstituted using standard Gen-Probe Inc. procedure. This mixture was allowed to incubate for one hour at 42° C. The reactions were then analyzed by the HPA procedure, as described above. The results of this test are reported as RLU in Table 2, and labeled AMP Pellets(+). As above, negative control reactions were run without nucleic acid (−).

The prepared enzyme pellets were tested by heating 100 µl of a combination of SDB with positive control nucleic acid, EDB, and the standard reconstituted amplification reagent (in a 2:1:1 ratio) at 95° C. for 10 minutes and then cooled to 42° C. for 5 minutes. The total volume of the reaction mix was added to the prepared enzyme pellet. After the pellet was dissolved, the reaction was heated to 42° C. for one hour and then subjected to HPA analysis as above. The results of this test are reported as RLU in Table 2 below, labeled Enzyme Pellet (+). Control reactions were prepared using standard Gen-Probe Inc. reagents following standard procedure. Data reported as RLU, standard *C. Trachomatis* TMA/HPA reaction.

TABLE 2

Single dose aliquot of pelleted amplification and enzyme reagents

| Control (+) | Amp Pellets (+) | Amp Pellets (−) | Enzyme Pellets (+) | Enzyme Pellets (−) |
| --- | --- | --- | --- | --- |
| 2,363,342 | 2,451,387 | 2,619 | 2,240,989 | 3,418 |
| 2,350,028 | 2,215,235 | 2,358 | 3,383,195 | 1,865 |
| 2,168,393 | 2,136,645 | 3,421 | 2,596,041 | 2,649 |
| 2,412,876 | 2,375,541 | 2,247 | 2,342,288 | 1,653 |

The data in Table 2 demonstrates that there was no significant difference when using the standard Gen-Probe Inc. reagents, or the dried, prepared, single dose amplification reagent pellet, or the enzyme reagent pellet. Thus the single dose aliquots of reagents are suitable for use with a single unified buffer for application to automation using a VIDAS system.

EXAMPLE 2

Automated Isothermal Amplification Using Thermolabile Enzymes

In order to automate the isothermal amplification assay reaction for use with clinical assay apparatus, such as a VIDAS instrument (BioMérieux Vitek, Inc.), a novel dual-chamber reaction vessel has been designed to implement the use of the unified buffer and single reaction aliquot reagent pellets described above in isothermal amplification assay of test samples which can be further used in combination with a stand alone processing station.

A) Dual reaction chambers

Figure 3A:
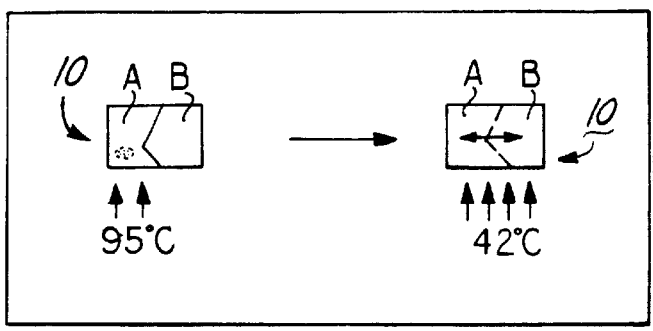
FIG. 3A is a schematic representation of a disposable dual chamber reaction vessel and the heating steps associated therewith to perform a TMA reaction in accordance with one possible embodiment of the invention.

The use of two chambers will facilitate keeping separate the heat stable sample/amplification reagent (containing the specific primers and nucleotides) from the heat labile enzymatic components (i.e. RNA reverse transcriptase, RNA polymerase RNase H). FIG. 3A is a schematic representation of a disposable dual chamber reaction vessel 10 and the heating steps associated therewith to perform a TMA reaction in accordance with one possible embodiment of the invention. Chamber A contains the amplification mix, namely deoxynucleotides, primers, $MgCl_2$ and other salts and buffer components. Chamber B contains the amplification enzyme that catalyzes the amplification reaction, e.g., T7 and/or RT. After addition of the targets (or patient sample) into chamber A, heat is applied to chamber A to denature the DNA nucleic acid targets and/or remove RNA secondary structure. The temperature of chamber A is then cooled down to allow primer annealing. Subsequently, the solution of chamber A is brought into contact with chamber B. Chambers A and B, now in fluid communication with each other, are then maintained at the optimum temperature for the amplification reaction, e.g., 42 degrees C. By spatially separating chamber A from chamber B, and applying the heat for denaturation to chamber A only, the thermolabile enzymes in chamber B are protected from inactivation during the denaturation step.

Figure 3B:
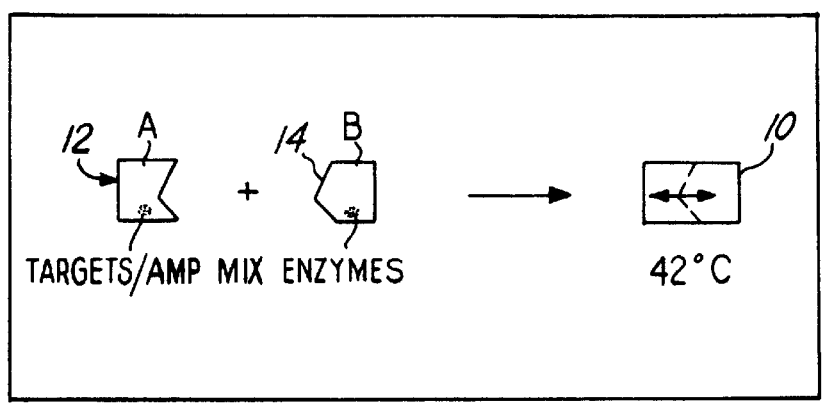
FIG. 3B is a schematic representation of alternative form of the invention in which two separate reaction chambers are combined to form a dual chamber reaction vessel.

FIG. 3B is a schematic representation of an alternative form of the invention in which two separate reaction chambers 12 and 14 are combined to form a dual chamber reaction vessel 10. Like the embodiment of FIG. 3A, Chamber A is pre-loaded during a manufacturing step with an amplification mix, namely nucleotides, primers, $MgCl_2$ and other salts and buffer components. Chamber B is pre-loaded during manufacturing with the amplification enzyme that catalyzes the amplification reaction, e.g., T7 and/or RT. Fluid sample is then introduced into chamber A. The targets are heated for denaturation to 95° C. in chamber A. After cooling chamber A to 42° C., the solution in chamber A is brought into contact with the enzymes in chamber B to trigger the isothermal amplification reaction.

If the reaction vessel is designed such that, after having brought the contents of chambers A and B into contact, the amplification chamber does not allow any exchange of materials with the environment, a closed system amplification is realized that minimizes the risk of contaminating the amplification reaction with heterologous targets or amplification products from previous reactions.

Figure 3C:
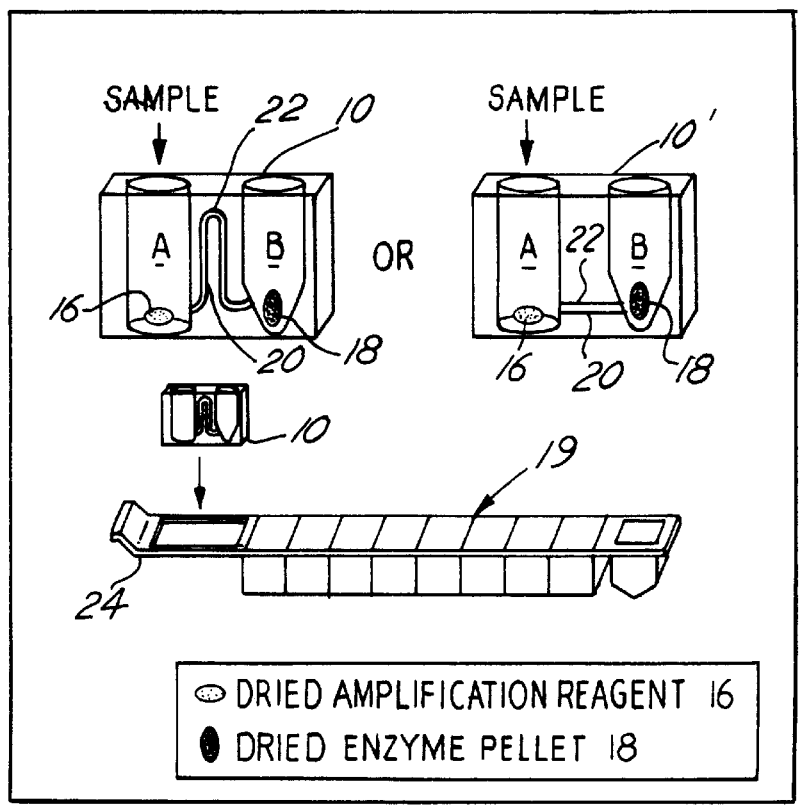
FIG. 3C is a schematic representation of two alternative embodiments of a dual chamber reaction vessel that are snapped into place in a test strip for processing with a solid phase receptacle and optical equipment in accordance with a preferred embodiment of the invention.

FIG. 3C is a schematic representation of two alternative dual chamber reaction vessels 10 and 10' that are snapped into place in a test strip 19 for processing with a solid phase receptacle and optical equipment in accordance with a preferred embodiment of the invention. In the embodiments of FIG. 3, a unidirectional flow system is provided. The sample is first introduced into chamber A for heating to the denaturation temperature. Chamber A contains the dried amplification reagent mix 16. After cooling, the fluid is transferred to chamber B containing the dried enzyme 18 in the form of a pellet. Chamber B is maintained at 42° C. after the fluid sample is introduced into Chamber B. The amplification reaction takes place in Chamber B at the optimum reaction temperature (e.g., 42° C.). After the reaction is completed, the test strip 19 is then processed in a machine such as the VIDAS® instrument available from bioMérieux Vitek, Inc., the assignee of the present invention. Persons of skill in the art are familiar with the VIDAS ® instriment.

The steps of heating and cooling of chamber A could be performed prior to the insertion of the dual chamber disposable reaction vessel 10 or 10' into the test strip 16, or, alternatively, suitable heating elements could be placed adjacent to the left hand end 24 of the test strip 19 in order to provide the proper temperature control of the reaction chamber A. The stand alone amplification processing station of FIGS. 4–14, described below, incorporates suitable heating elements and control systems to provide the proper temperature control for the reaction vessel 10.

Figure 4:
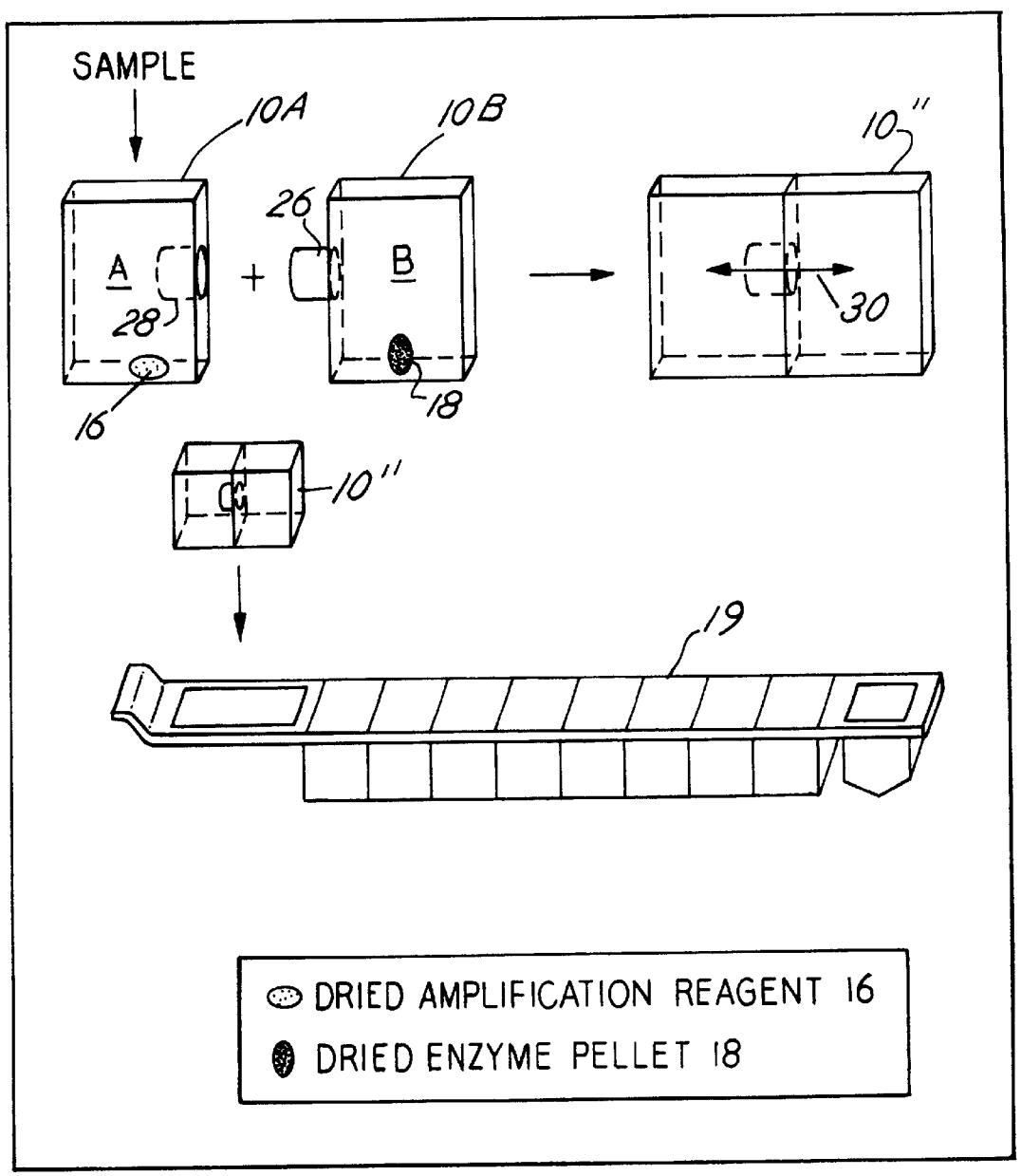
FIG. 4 is a schematic representation of an alternative embodiment of a dual chamber reaction vessel formed from two separate chambers that are combined in a manner to permit a fluid sample in one chamber to be transferred to the other chamber, with the combined dual chamber vessel placed into a test strip such as illustrated in FIG. 3C.

FIG. 4 is a schematic representation of an alternative embodiment of a dual chamber reaction vessel 10" formed from two separate interlocking vessels 10A and 10B that are combined in a manner to permit a fluid sample in one chamber to flow to the other, with the combined dual chamber vessel 10" placed into a test strip 19 such as described above in FIG. 3A. The fluid sample is introduced into chamber A, which contains the dried amplification reagent mix 16. Vessel A is then heated off-line to 95 degrees C, then cooled to 42 degrees C. The two vessels A and B are brought together by means of a conventional snap fit between complementary locking surfaces on the tube projection 26 on chamber B and the recessed conduit 28 on chamber A. The mixing of the sample solution from chamber A with the enzyme from chamber B occurs since the two chambers are in fluid communication with each other, as indicated by the arrow 30. The sample can then be amplified in the combined dual chamber disposable reaction vessel 10" off-line, or on-line by snapping the combined disposable vessel 10" into a modified VIDAS® strip. The VIDAS® instrument could perform the detection of the amplification reaction in known fashion.

B) Amplification Station

Figure 5:
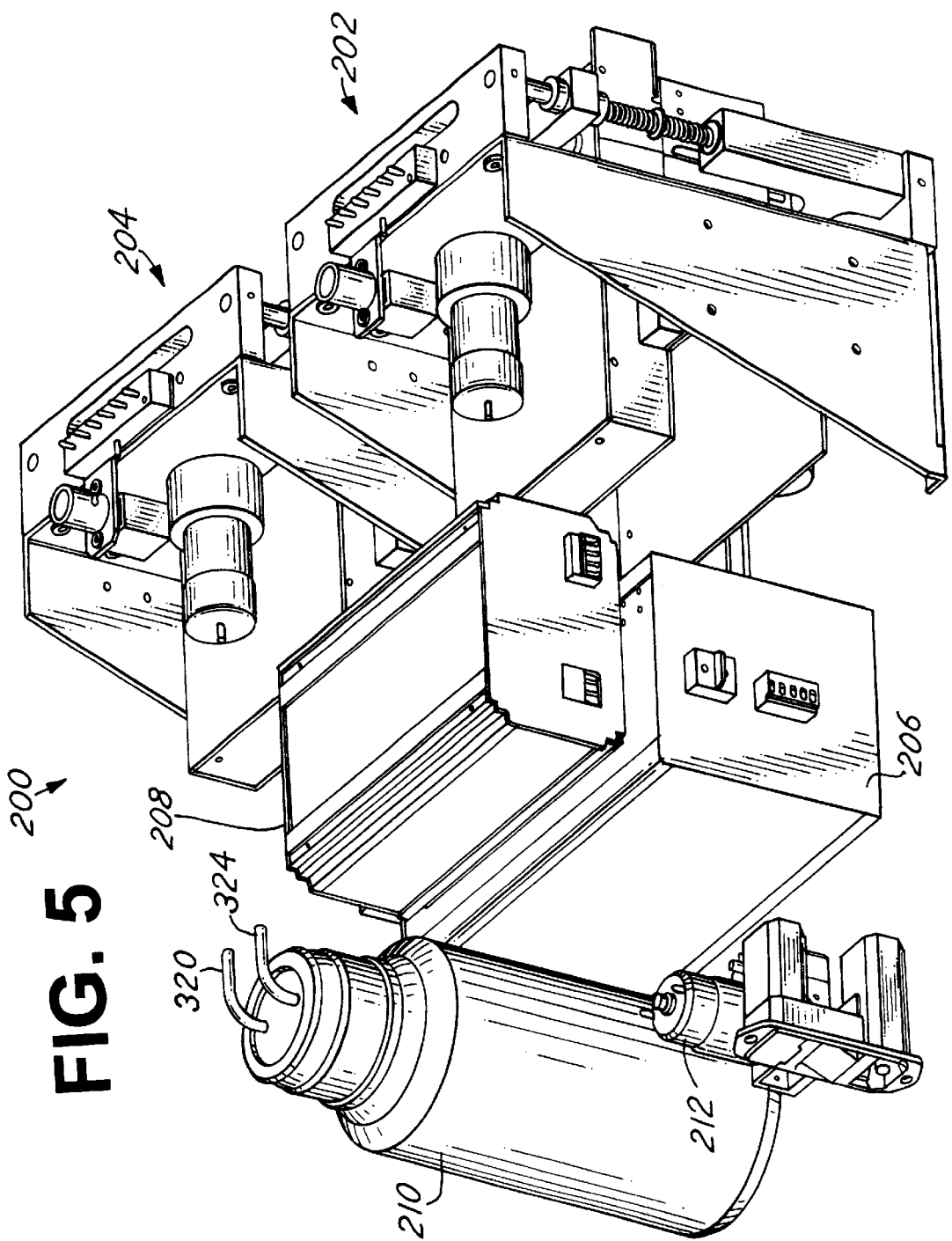
FIG. 5 is a perspective view of a stand-alone amplification processing station for the test strips having the dual chamber reaction vessels in accordance with a presently preferred form of the invention.

FIG. 5 is a perspective view of a stand-alone amplification processing system 200 for the test strips 19 having the dual chamber reaction vessels in accordance with a presently preferred form of the invention. The system 200 consists of two identical amplification stations 202 and 204, a power supply module 206, a control circuitry module 208, a vacuum tank 210 and connectors 212 for the power supply module 206. The tank 210 has hoses 320 and 324 for providing vacuum to amplification stations 202 and 204 and ultimately to a plurality of vacuum probes (one per strip) in the manner described above for facilitating transfer of fluid from the first chamber to the second chamber. The vacuum subsystem is described below in conjunction with FIG. 14.

The amplification stations 202 and 204 each have a tray for receiving at least one of the strips and associated temperature control, vacuum and valve activation subsystems for heating the reaction wells of the strip to the proper temperatures, transferring fluid from the first chamber in the dual chamber reaction wells to the second chamber, and activating a valve such as a thimble valve to open the fluid channel to allow the fluid to flow between the two chambers.

The stations 202 and 204 are designed as stand alone amplification stations for performing the amplification reaction in an automated manner after the patient or clinical sample has been added to the first chamber of the dual chamber reaction vessel described above. The processing of the strips after the reaction is completed with an SPR takes place in a separate machine, such as the VIDAS® instrument. Specifically, after the strips have been placed in the stations 202 and 204 and the reaction run in the stations, the strips are removed from the stations 202 and 204 and placed into a VIDAS® instrument for subsequent processing and analysis in known fashion.

The entire system 200 is under microprocessor control by an amplification system interface board (not shown in FIG. 5). The control system is shown in block diagram form in FIG. 12 and will be described later.

Figure 6:
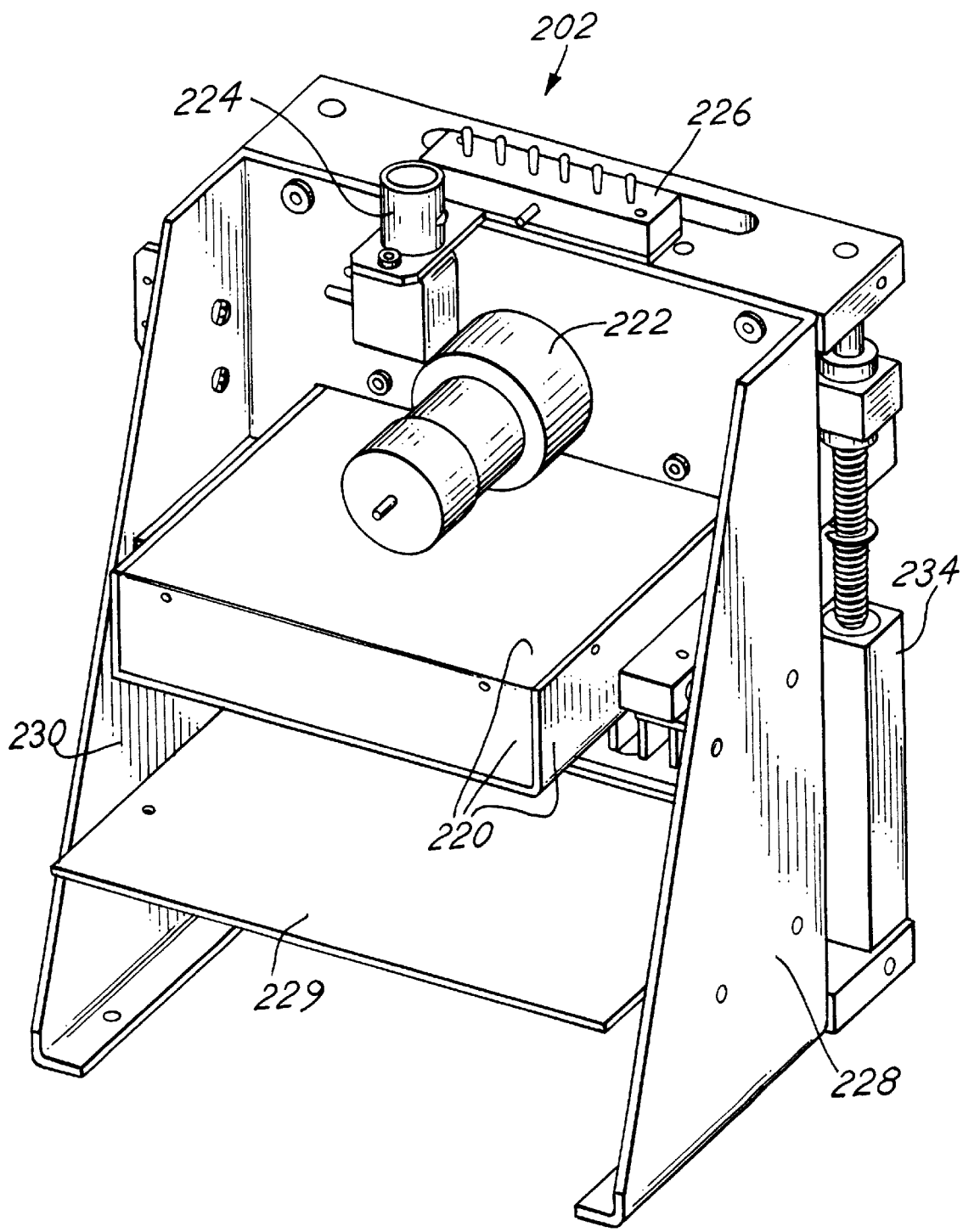
FIG. 6 is a perspective view of one of the amplification modules of FIG. 4/31, as seen from the rear of the module.
Figure 7:
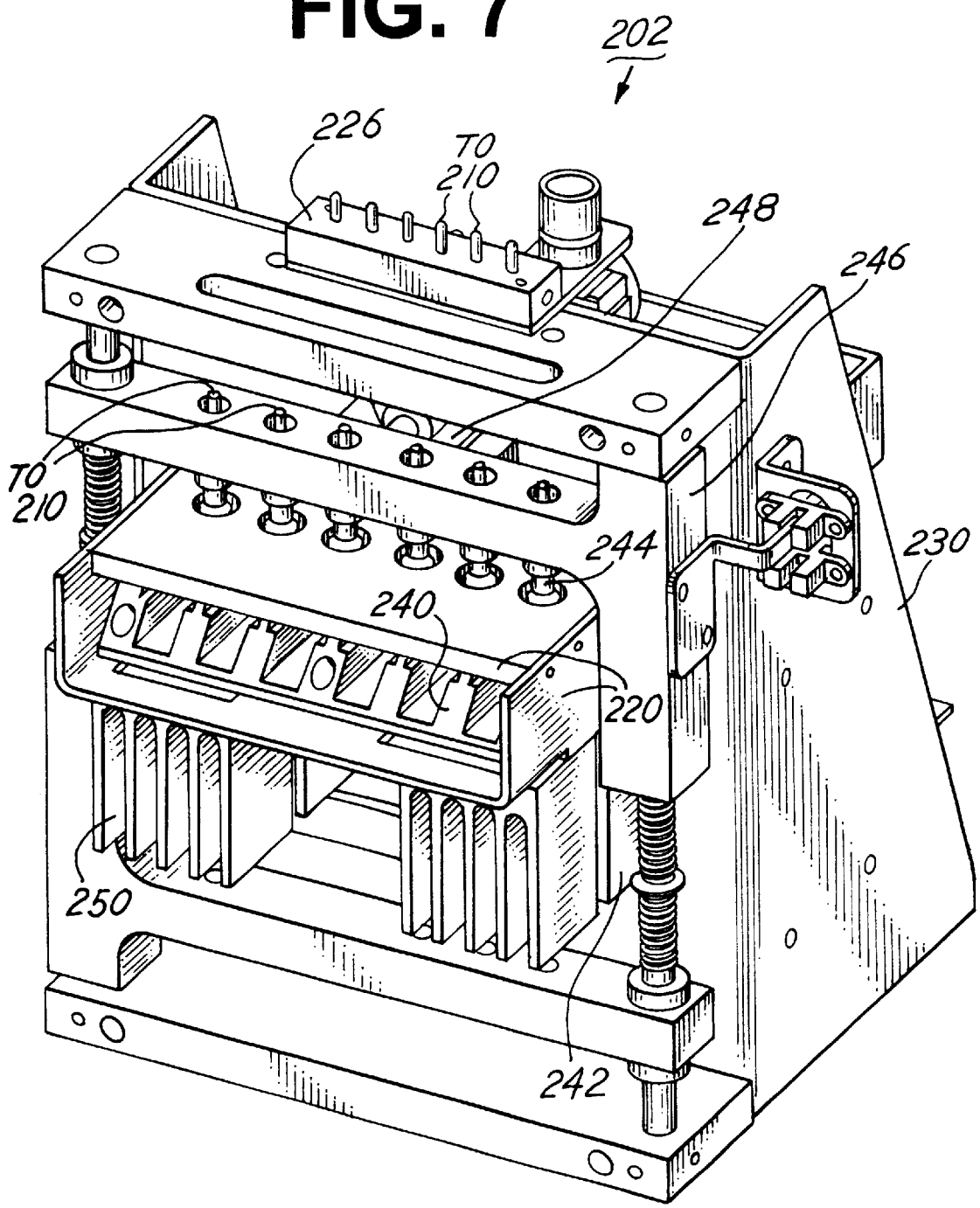
FIG. 7 is a perspective view of the front of the module of FIG. 5/32.

Referring now to FIG. 6, one of the amplification stations 202 is shown in a perspective view. The other amplification station is of identical design and construction. FIG. 7 is a perspective view of the front of the module of FIG. 6.

Referring to these figures, the station includes a vacuum probe slide motor 222 and vacuum probes slide cam wheel 246 that operate to slide a set of vacuum probes 244 (shown in FIG. 7) for the thimble valves up and down relative to a vacuum probes slide 246 to open the thimble valves and apply vacuum so as to draw the fluid from the first chamber of the reaction vessel 10 to the second chamber. The vacuum probes 244 reciprocate within annular recesses provided in the vacuum probes slide 246. Obviously, proper registry of the pin structure and vacuum probe 244 with corresponding structure in the test strip as installed on the tray needs to be observed.

The station includes side walls 228 and 230 that provide a frame for the station 202. Tray controller board 229 is mounted between the side walls 228 and 230. The electronics module for the station 202 is installed on the tray controller board 229.

A set of tray thermal insulation covers 220 are part of a thermal subsystem and are provided to envelop a tray 240 (FIG. 7) that receives one or more of the test strips. The insulation covers 220 help maintain the temperature of the tray 240 at the proper temperatures. The thermal subsystem also includes a 42° C. Peltier heat sink 242, a portion of which is positioned adjacent to the second chamber in the dual chamber reaction vessel in the test strip to maintain that chamber at the proper temperature for the enzymatic amplification reaction. A 95° C. heat sink 250 is provided for the front of the tray 240 for maintaining the first chamber of the reaction well in the test strip at the denaturation temperature.

Figure 8:
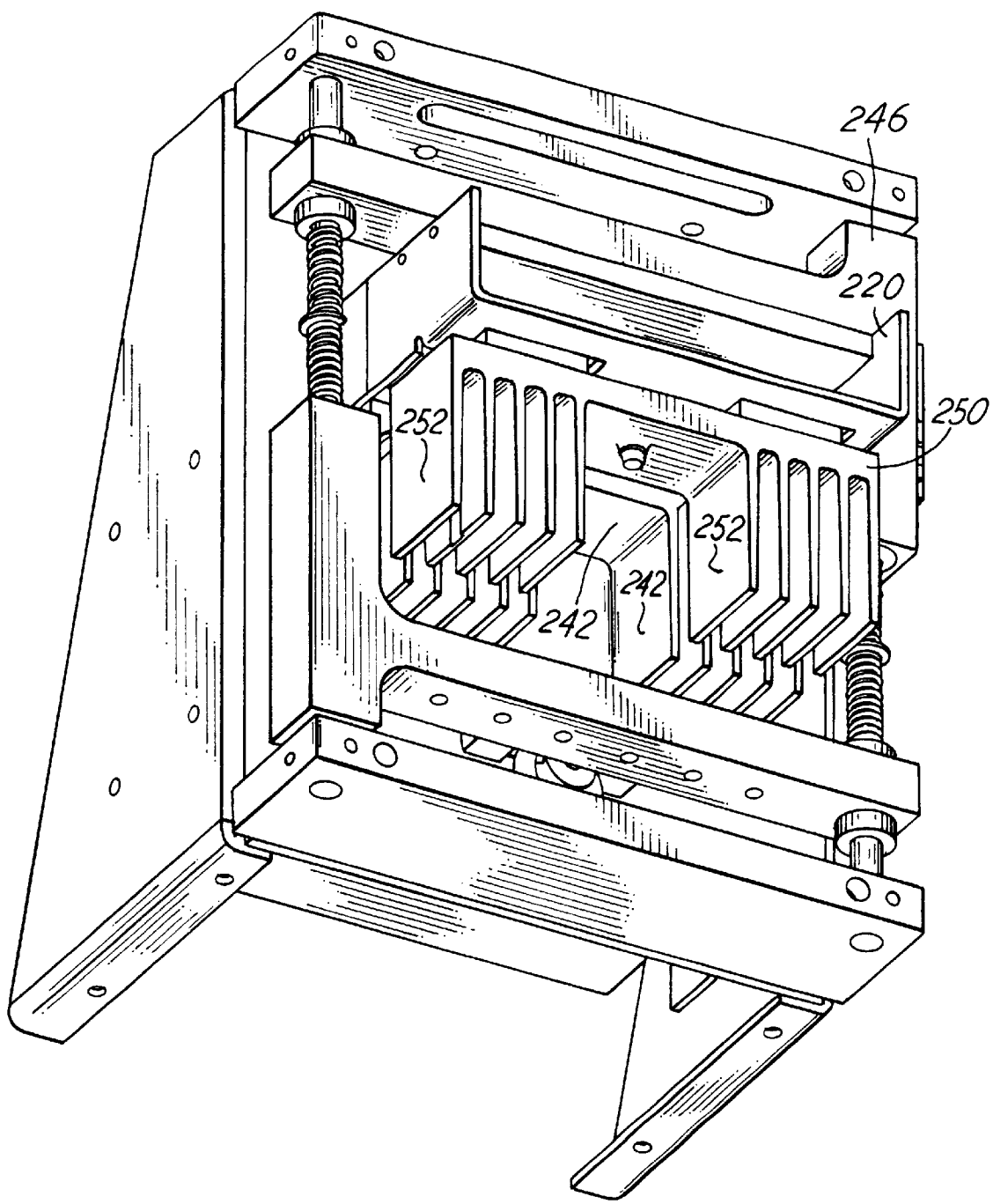
FIG. 8 is another perspective view of the module of FIG. 7.

FIG. 8 is another perspective view of the module of FIG. 7, showing the 95° C. heat sink 250 and a set of fins 252. Note that the 95° C. heat sink 250 is positioned to the front of and slightly below the tray 240. The 42° C. heat sink 242 is positioned behind the heat sink 250.

Figure 9:
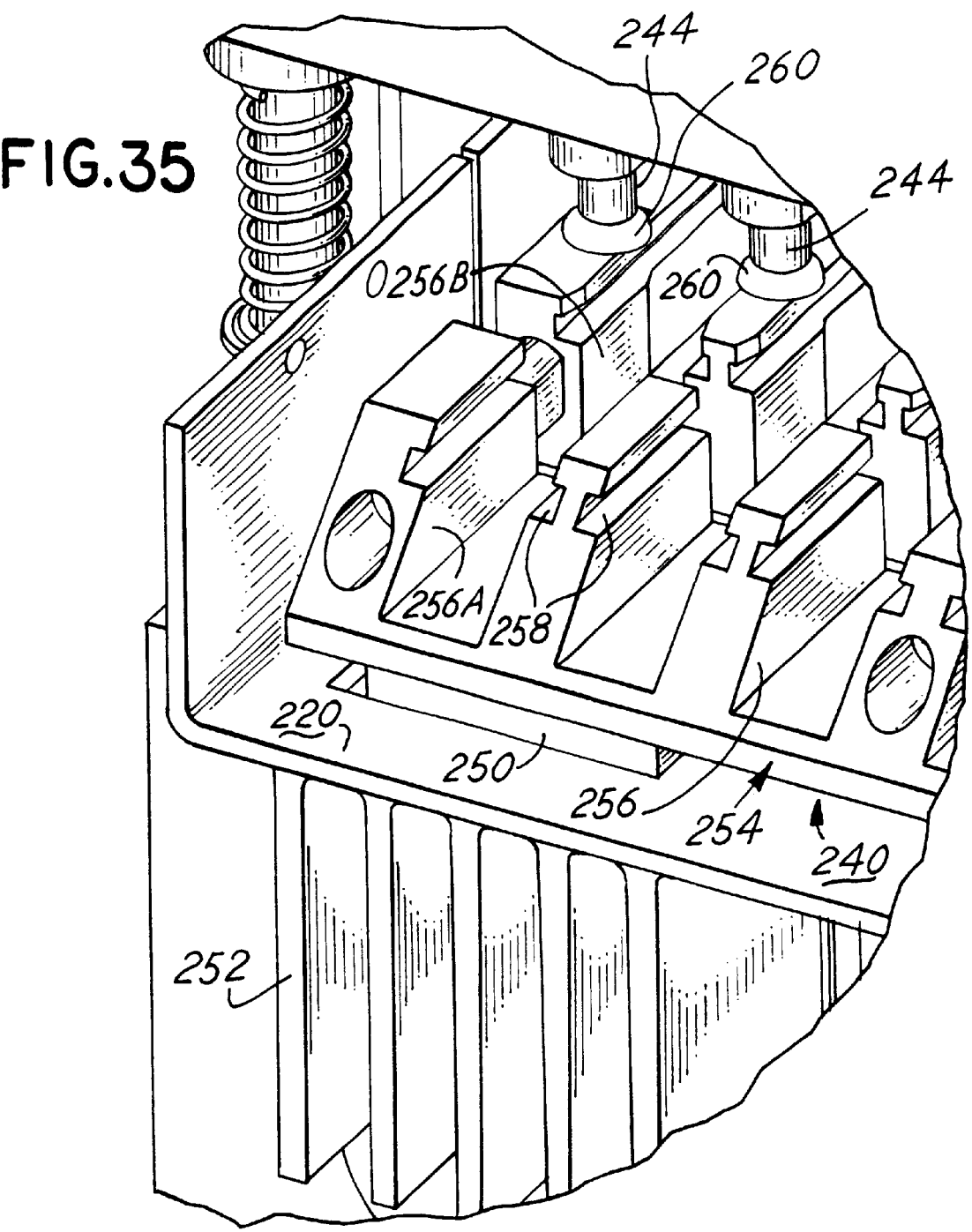
FIG. 9 is a detailed perspective view of a portion of the test strip holder and 95° C. Peltier heating subsystems of the module of FIGS. 6–8.

FIG. 9 is a detailed perspective view of a portion of the tray 240 that holds the test strips (not shown) as seen from above. The tray 240 includes a front portion having a base 254, a plurality of discontinuous raised parallel ridge structures 256 with recessed slots 258 for receiving the test strips. The base of the front 254 of the tray 240 is in contact with the 95° C. heat sink 250. The side walls of the parallel raised ridges 256 at positions 256A and 256B are placed as close as possible to the first and second chambers of the reaction vessel 10 of FIG. 3A so as to reduce thermal resistance. The base of the rear of the tray 240 is in contact with a 42° C. Peltier heat sink, as best seen in FIG. 8. The portion 256B of the raised ridge for the rear of the tray is physically isolated from portion 256A for the front of the tray, and portion 256B is in contact with the 42° C. heat sink so as to keep the second chamber of the reaction vessel in the test strip at the proper temperature.

Still referring to FIG. 9, the vacuum probes 244 include a rubber gasket 260. When the vacuum probes 244 are lowered by the vacuum probe motor 222 (FIG. 6) the gaskets 260 are positioned on the upper surface of the test strip surrounding the vacuum port in the dual chamber reaction vessel so as to make a tight seal and permit vacuum to be drawn on the second chamber.

Figure 10:
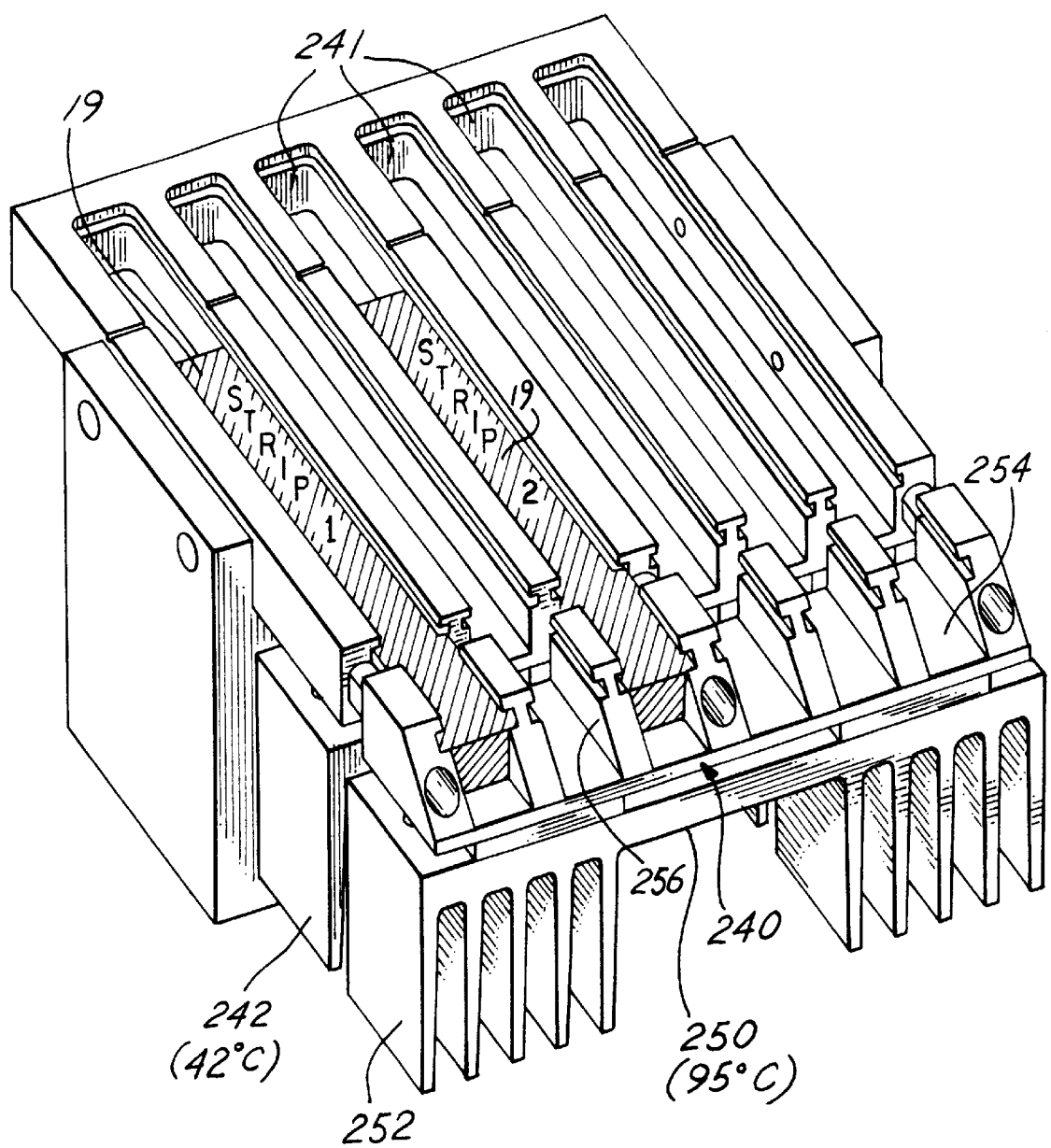
FIG. 10 is an isolated perspective view of the test strip holder of FIG. 9, showing two test strips installed in the test strip holder.

FIG. 10 is an isolated perspective view of the test strip holder or tray 240 of FIG. 9, showing two test strips installed in the tray 240. The tray 240 has a plurality of lanes or slots 241 receiving up to six test strips 19 for simultaneous processing. FIG. 10 shows the heat sinks 242 and 250 for maintaining the respective portions of the tray 240 and ridges 256 at the proper temperature.

Figure 11:
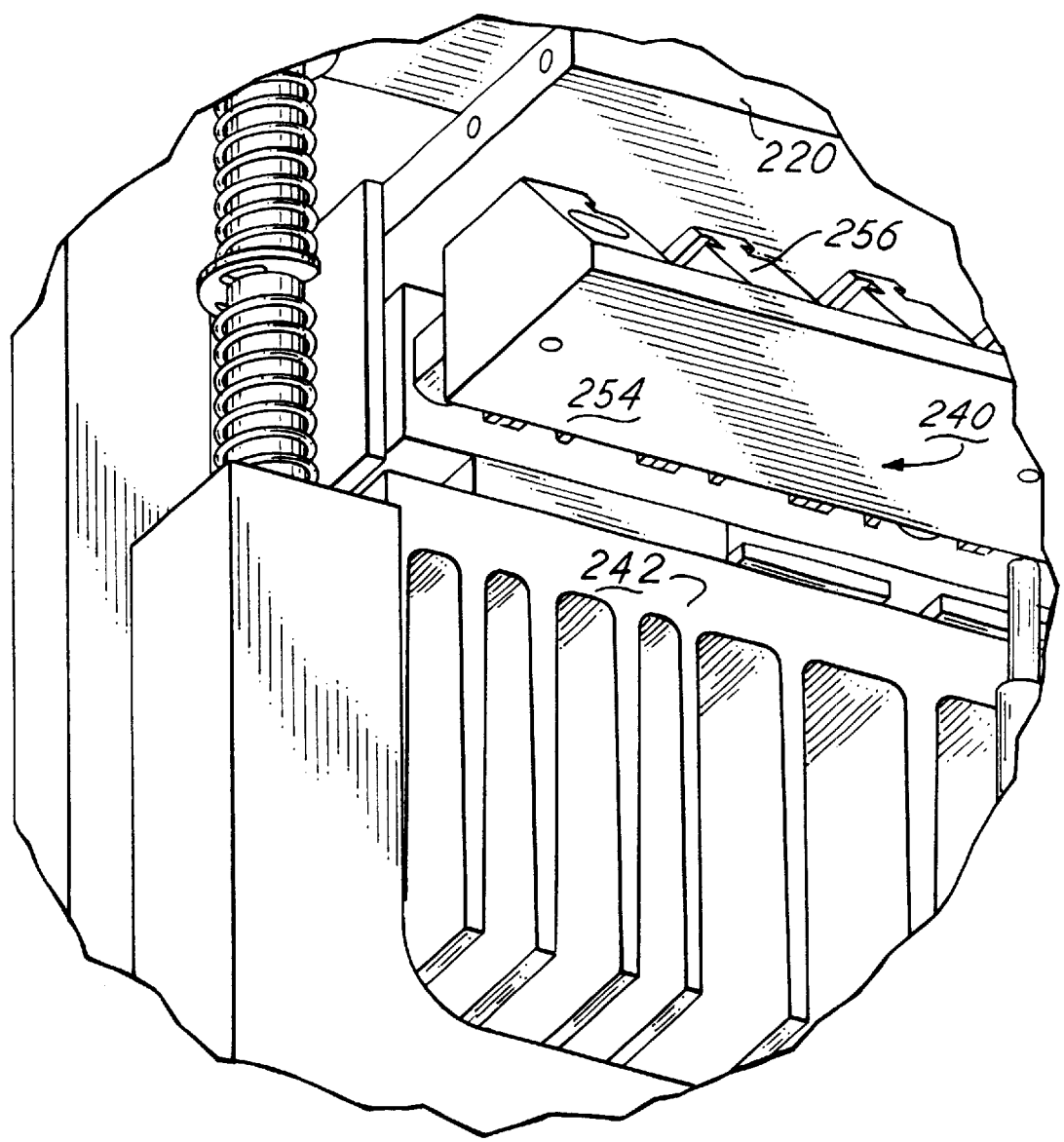
FIG. 11 is a detailed perspective view of the test strip holder or tray of FIG. 7.

FIG. 11 is a detailed perspective view of the test strip holder or tray 240 as seen from below. The 95° C. Peltier heat sink which would be below front portion 254 has been removed in order to better illustrate the rear heat sink 242 beneath the rear portion of the tray 240.

Figure 12:
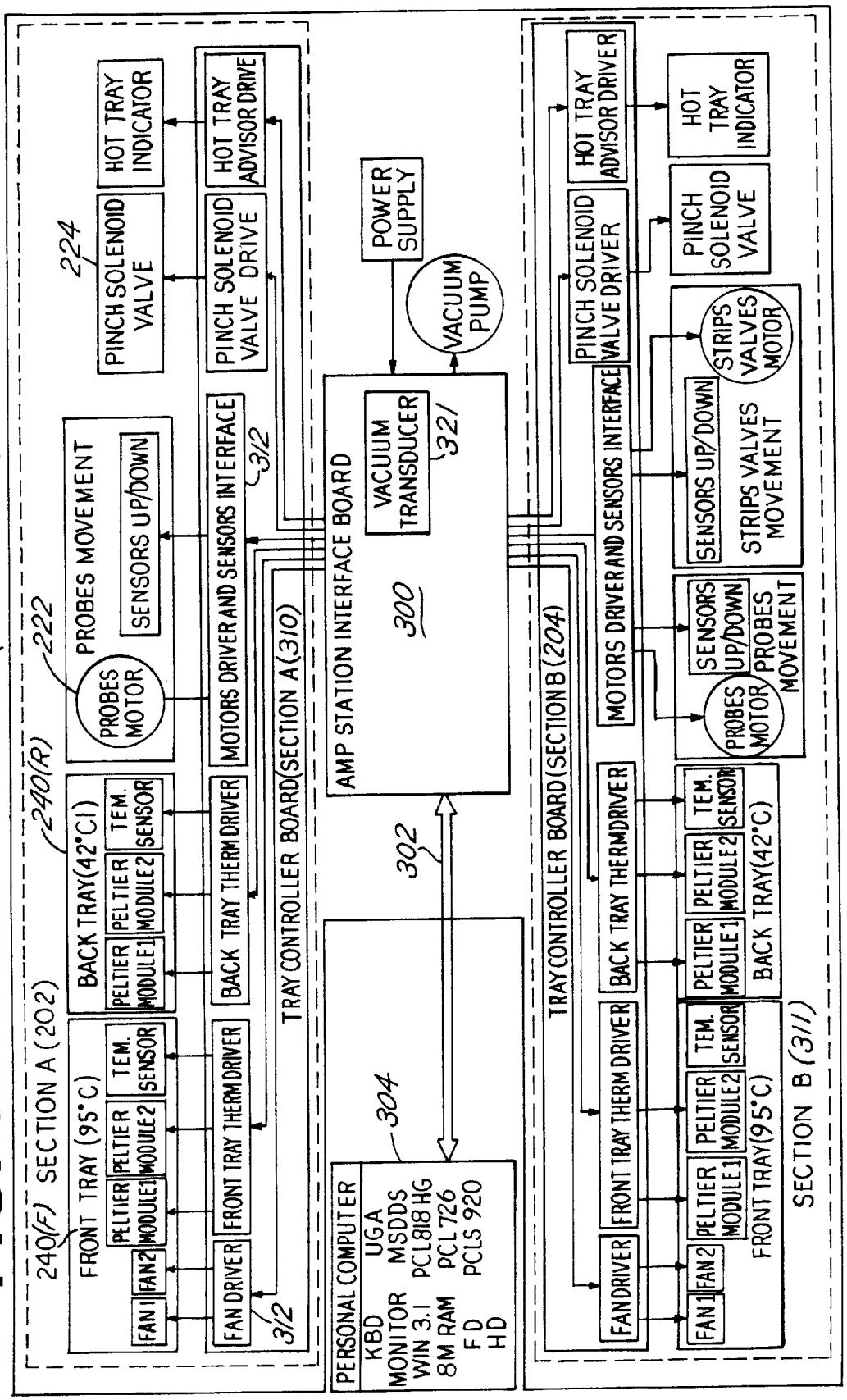
FIG. 12 is a block diagram of the electronics of the amplification processing station of FIG. 7.

FIG. 12 is a block diagram of the electronics and control system of the amplification processing system of FIG. 5. The control system is divided into two boards 310 and 311, section A 310 at the top of the diagram devoted to amplification module or station 202 and the other board 311 (section B) devoted to the other module 204. The two boards 310 and 311 are identical and only the top section 310 will be discussed. The two boards 310 and 311 are connected to an amplification station interface board 300.

The interface board 300 communicates with a stand alone personal computer 304 via a high speed data bus 302. The personal computer 304 is a conventional IBM compatible computer with hard disk drive, video monitor, etc. In a preferred embodiment, the stations 202 and 204 are under control by the interface board 300.

The board 310 for station 202 controls the front tray 240 which is maintained at a temperature of 95° C. by two Peltier heat sink modules, a pair of fans and a temperature sensor incorporated into the front portion 254 of the tray 240. The back of the tray is maintained at a temperature of 42° C. by two Peltier modules and a temperature sensor. The movement of the vacuum probes 244 is controlled by the probes motor 222. Position sensors are provided to provide input signals to the tray controller board as to the position of the vacuum probes 244. The tray controller board 310 includes a set of drivers 312 for the active and passive components of the system which receive data from the temperature and position sensors and issue commands to the active components, i.e., motors, fans, Peltier modules, etc. The drivers are responsive to commands from the amplification interface board 300. The interface board also issues commands to the vacuum pump for the vacuum subsystem, as shown.

Figure 13:
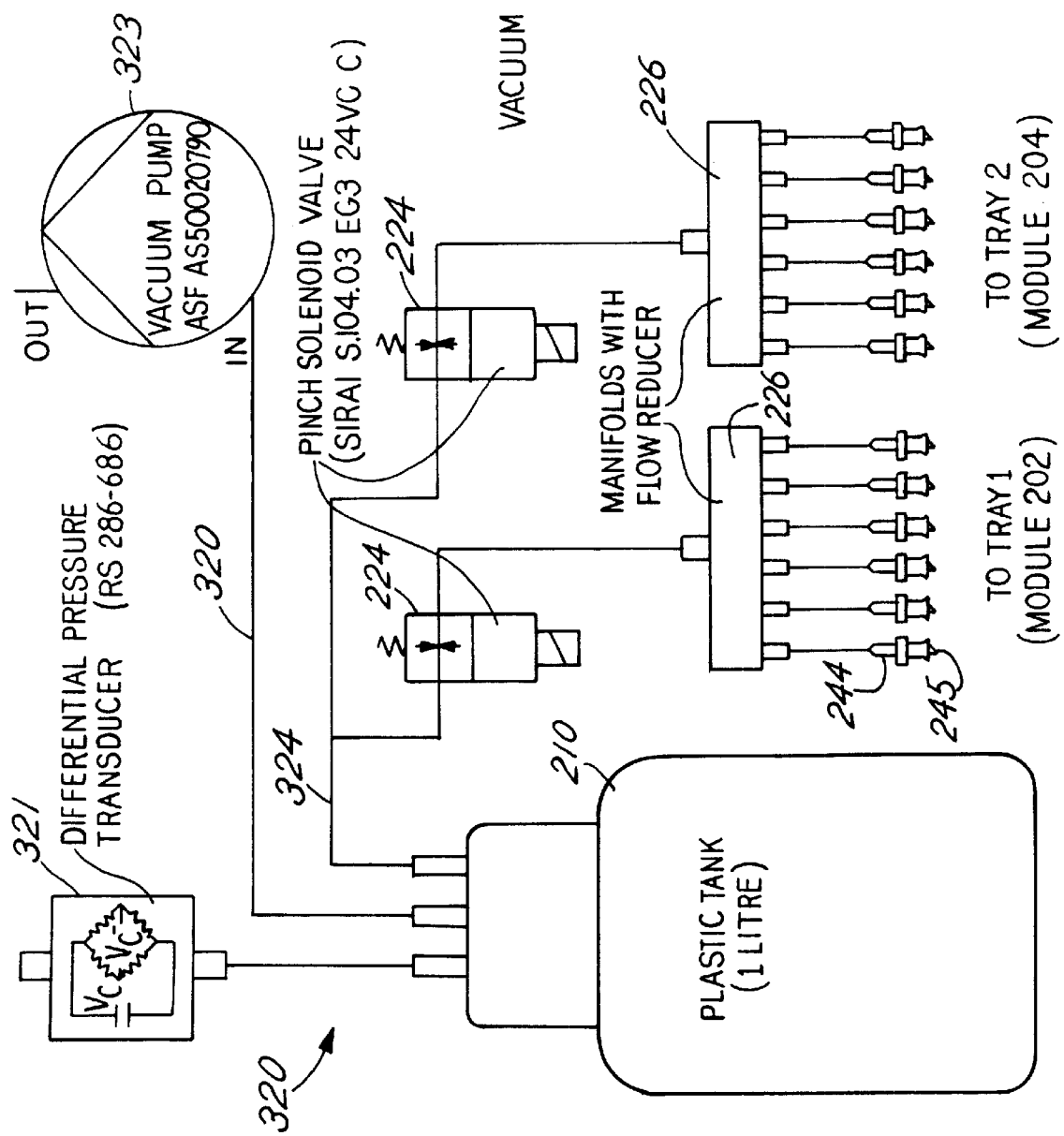
FIG. 13 is a diagram of the vacuum subsystem for the amplification processing station of FIG. 6.

FIG. 13 is a diagram of the vacuum subsystem 320 for the amplification processing stations 202 and 204 of FIG. 5. The subsystem includes a 1 liter plastic vacuum tank 210 which is connected via an inlet line 322 to a vacuum pump 323 for generating a vacuum in the tank 210. A vacuum supply line 324 is provided for providing vacuum to a pair of pinch solenoid valves 224 (see FIG. 6) via supply lines 324A and 324B. These vacuum supply lines 324A and 324B supply vacuum to a manifold 226 distributing the vacuum to the vacuum probes 244. Note the pointed tips 245 of the vacuum probes 244 for piercing the film or membrane 64 covering the strip 19. The vacuum system 320 also includes a differential pressure transducer 321 for monitoring the presence of vacuum in the tank 210. The transducer 321 supplies pressure signals to the interface board 300 of FIG. 12.

Figure 14:
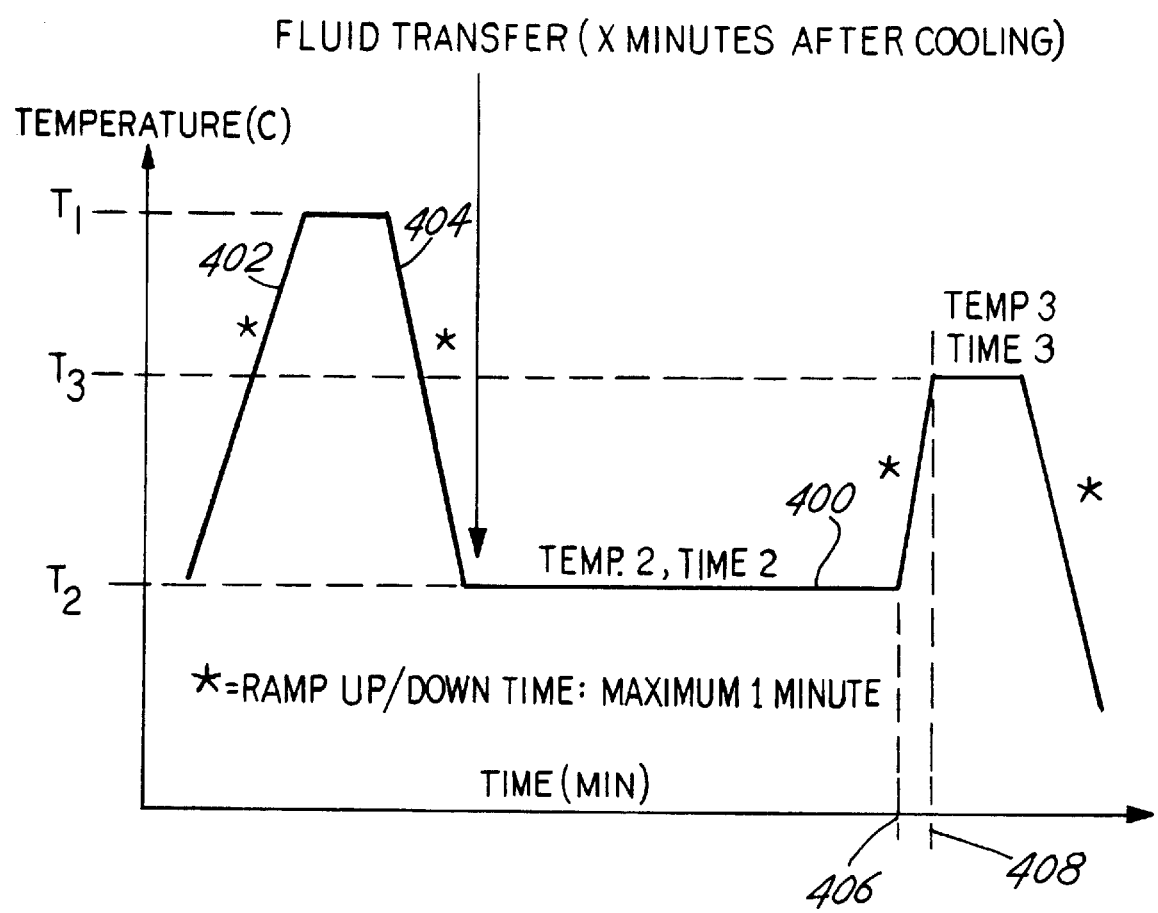
FIG. 14 is a graph of the thermal cycle of the station of FIG. 6.

FIG. 14 is a representative graph of the thermal cycle profile of the station of FIG. 5. As indicated in line 400, after an initial ramp up 402 in the temperature lasting less than a minute, a first temperature T1 is reached (e.g., a denaturation temperature) which is maintained for a predetermined time period, such as 5–10 minutes, at which time a reaction occurs in the first chamber of the reaction vessel. Thereafter, a ramp down of temperature as indicated at 404 occurs and the temperature of the reaction solution in the first chamber of the reaction vessel 10 cools to temperature T2. After a designated amount of time after cooling to temperature T2, a fluid transfer occurs in which the solution in the first chamber is conveyed to the second chamber. Temperature T2 is maintained for an appropriate amount of time for the reaction of interest, such as one hour. At time 406, the temperature is raised rapidly to a temperature T3 of 65° C. to stop the amplification reaction. For a TMA reaction, it is important that the ramp up time from time 406 to time 408 is brief, that is, less than 2 minutes and preferably less than one minute. Preferably, all the ramp up and ramp down of temperatures occur in less than a minute.

Other embodiments of reaction vessels and amplification station components are also envisioned, and certain examples of such alternative embodiments are described in copending U.S. patent application of Luigi Catanzariti et al., Ser. No. 08/850,207 hereby incorporated by reference in the entirety.

EXAMPLE 3

Automated VIDAS Test for Non-amplified and Amplified Detection of *Mycobacterium tuberculosis* (Mtb)

Using the VIDAS instrument (BioMérieux Vitek, Inc.), modified to 42° C., we have developed an in-line simple rapid nucleic acid amplification and detection assay for the clinical laboratory for the detection of Mtb in test samples which can be completed in a short time. The entire assay is designed to take place on a single test strip, minimizing the potential for target or amplicon contamination. The amplification based assay is capable of detection of Mtb where the sample contains only 5 cells similar to the sensitivity achieved by the Gen-Probe commercial kit.

The amplification based assay utilizes isothermal transcription-mediated amplification (TMA) targeting unique sequences of rRNA, followed by hybridization and enzyme-linked fluorescent detection of nucleic acid probe in the VIDAS instrument.

The amplification/detection assay can detect approximately 1 fg of Mtb rRNA, or less than one Mtb organism per test, and is specific for all members of the Mtb complex. Specific probes for the detection of Mtb can be found in C. Mabilat, 1994, J. Clin. Microbiol. 32, 2707.

Standard smears for acid-fast bacilli are not always reliable as a diagnostic tool, and even when positive may be a mycobateria other than Mtb. Currently, standard methods for diagnosis of tuberculosis requires culturing the slow-growing bacteria, and may take up to 6 weeks or longer. During this time, the patient is usually isolated. Initial results are that this automated test matches or exceeds the clinical sensitivity of the culture method, and offers a highly sensitive method to rapidly (in less than three hours) detect Mtb in infected samples, thereby aiding rapid diagnosis, isolation and treatment.

A) Sample Preparation

A 450 µl volume of specimen is added to 50 µl of specimen dilution buffer in a lysing tube containing glass beads, sonicated for 15 minutes at room temperature to lyse organisms, heat inactivated for 15 minutes at 95° C. Where required, isothermal amplification was conducted as per a commercially available manual assay kit (Gen-Probe Inc.) following the kit instructions using standard kit reagents. However, similar assays can be conducted using the modified components as described in the Examples above.

B) Detection

In order for the automated detection assay to operate, the detection system requires hybridization of the target nucleic acid or amplicon to a specific capture nucleic acid bound to a solid support, (in the VIDAS system called a "solid phase receptacle" SPR® pipet-like devise), and to a labeled detection probe nucleic acid (for example where the label can be alkaline phosphatase, a chemiluminescent signal compound, or other reagent that will allow for specific detection of bound probe).

In an automated system such as the VIDAS, after several wash steps to remove unbound probe, the SPR® transfers the probe-target hybrid to an enzyme substrate, whereby the detectable signal is triggered from the bound probe and detected by the assay instrument. In one embodiment, the probe is conjugated to alkaline phosphatase, and once placed in contact with substrate of methyl umbelliferyl phosphate (MUMP), the substrate is converted into 4-methyl umbelliferone (4-MU) by the alkaline phosphatase. The 4-MU produces fluorescence which is measured and recorded by the standard VIDAS instrument as relative fluorescence units (RFU). When target nucleic acid is not present, no probe is bound, and no substrate is converted, thus no fluorescence is detected.

C) Analytical sensitivity: Controls

Generally controls are prepared in a matrix of specimen dilution buffer with positive controls containing 5 fg of Mtb rRNA, or the equivalent rRNA of approximately 1 M tb cell. Sensitivity of the automated probe assay can be determined by testing dilutions of lysed M. tb cells. The cell lysates can generally be prepared with a 1 µl loop of cells (the assumption being that there are approximately $1\times10^9$ colony forming units (CFU) per 1 µl loop-full, based upon previous titration and CFU experiments). Dilutions of the Mtb lysates can then be tested with the automated probe assay.

Figure 20A:
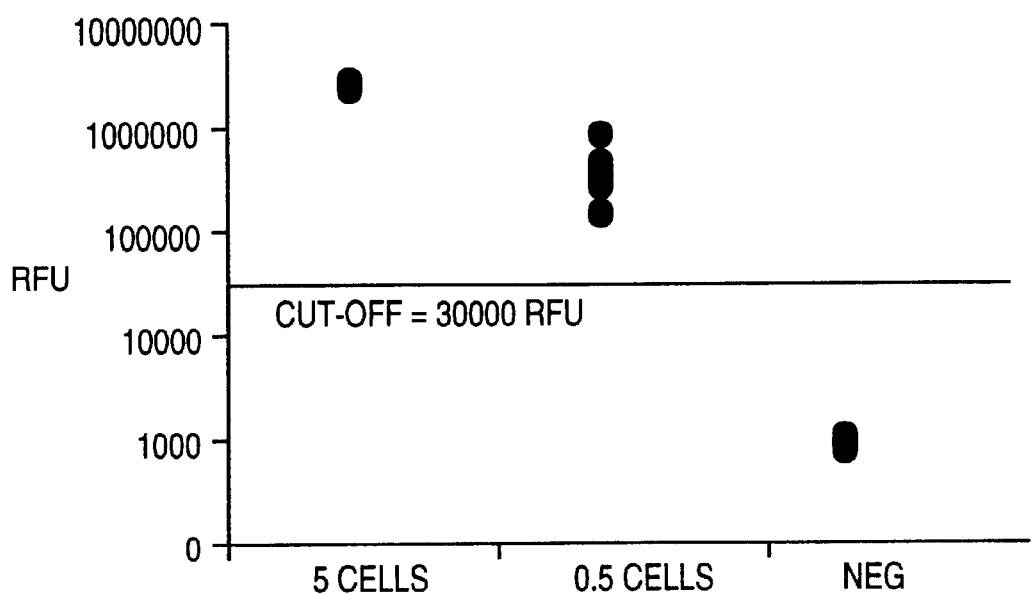
FIG. 20A is a graph showing detection of Mtb nucleic acid by VIDAS apparatus after amplification.
Figure 20B:
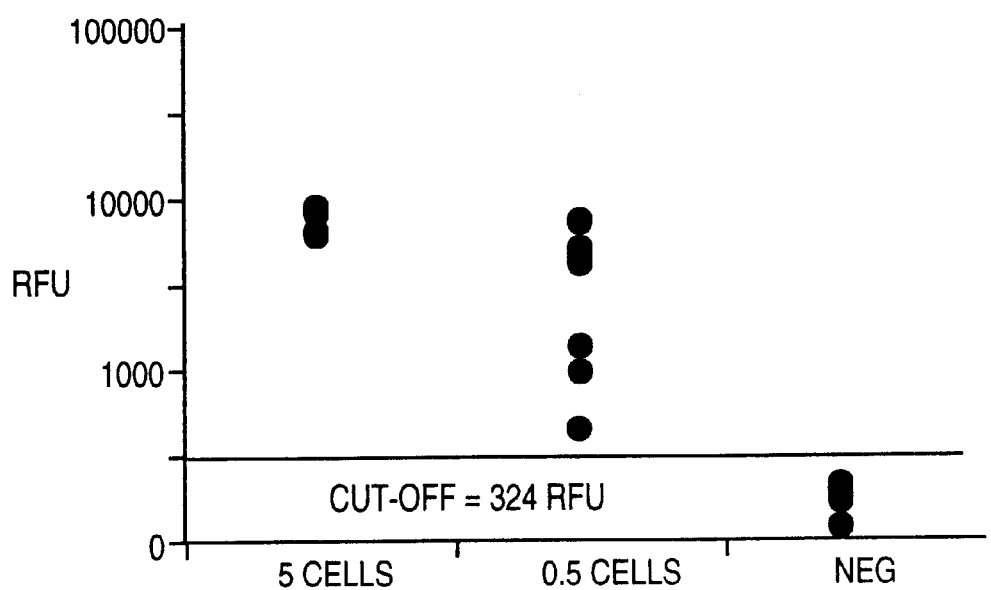
FIG. 20B is a graph showing detection of Mtb nucleic acid by VIDAS apparatus.

FIG. 20A is a graph showing detection of Mtb amplicons according to the Gen-Probe kit. FIG. 20B is a graph showing detection of Mtb amplicons from the same reactions as in FIG. 20A by the VIDAS instument.

Figure 21:
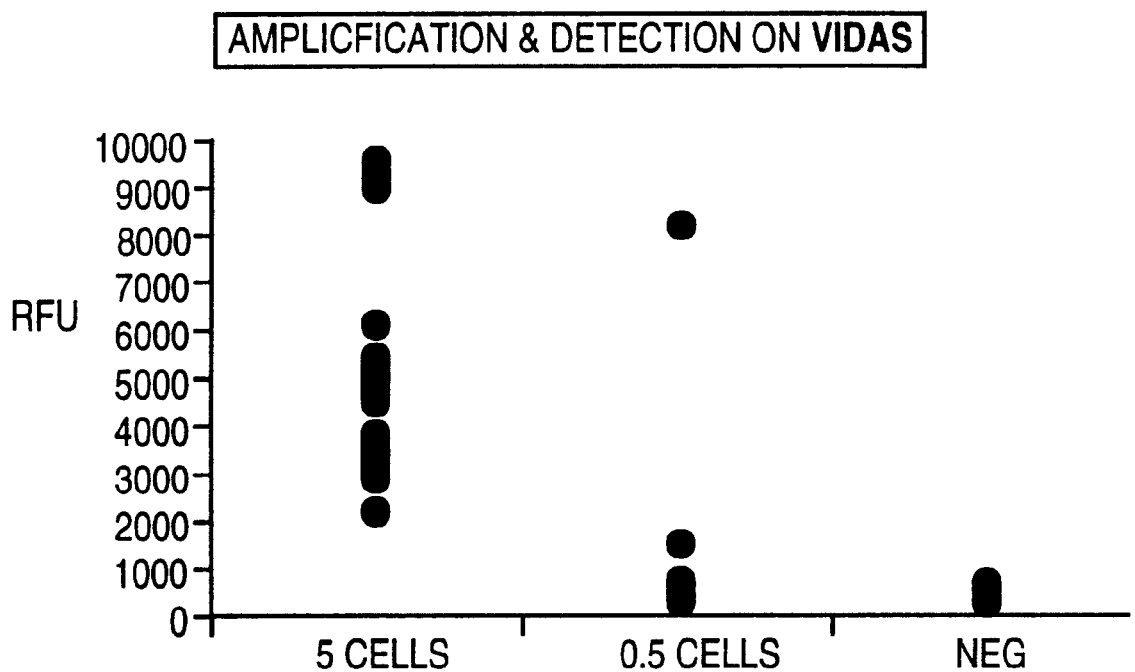
FIG. 21 is a graph showing detection of Mtb nucleic acid by VIDAS apparatus after amplification.

FIG. 21 is a graph showing amplification and detection of Mtb nucleic acids on the modified VIDAS apparatus. Enzyme was used in liquid form and amplification was performed in-line with VIDAS assay instument.

Figure 22:
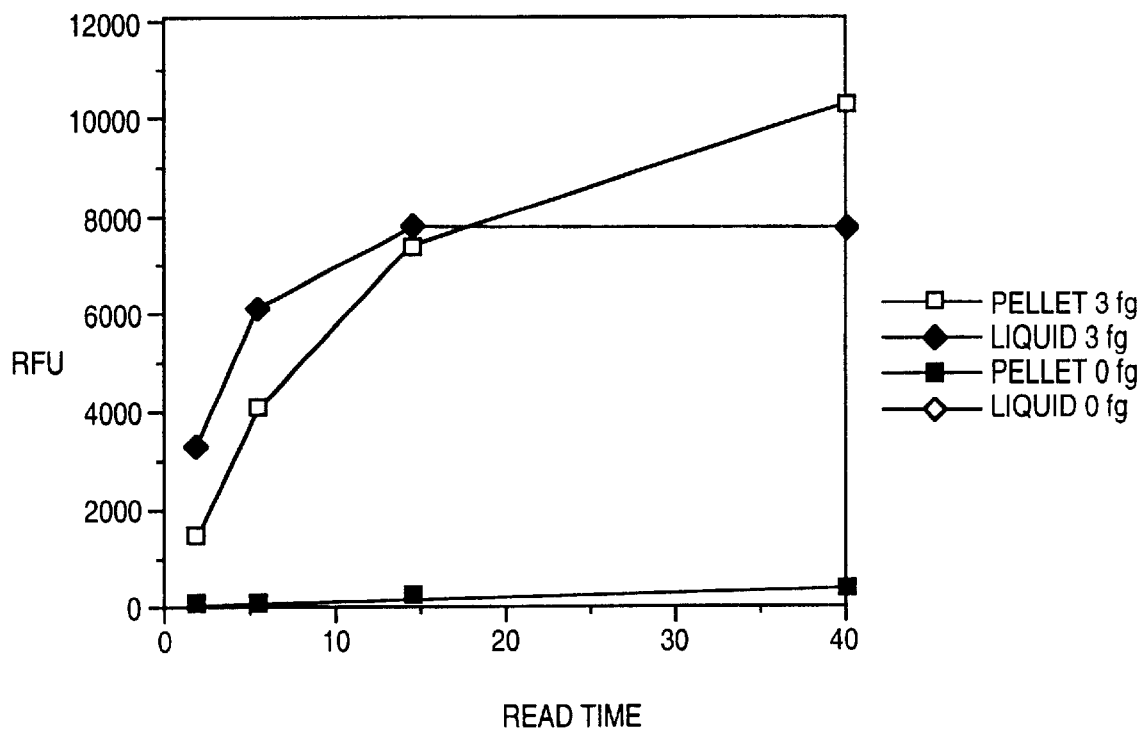
FIG. 22 is a graph showing detection of Mtb nucleic acid by VIDAS apparatus after amplification using the binary/dual chamber protocol.

FIG. 22 is a graph showing amplification and detection of Mtb nucleic acids on the modified VIDAS apparatus using the binary/dual chamber disposable reaction vessel. The denaturation step was performed off-line of the VIDAS instrument, amplification and detection was performed in-line with VIDAS instrument.

EXAMPLE 4

Automated VIDAS Test for Amplified Detection of *Chlamydia trachomatis* (CT)

Using the VIDAS instrument (BioMérieux Vitek, Inc.), we have developed a simple, fully automated, highly specific assay for the rapid detection of *Chlamydia trachomatis* (CT) from test samples. The test utilizes isothermal TMA targeting unique sequences of the rRNA followed by hybridization and enzyme-linked fluorescence detection. The automated test specifically detects all the clinically important serovars of *Chlamydia trachomatis* (CT) from urogenital specimens in less than two hours. We obtained an analytical sensitivity of 0.5 fg of rRNA, or the equivalent of approximately $1/10^{th}$ of an elementary body of *Chlamydia trachomatis* (CT). Agreement between the automated test and Gen-Probe's Amplified CT test for 207 clinical endocervical swabs and urines showed complete agreement.

*Chlamydia trachomatis* (CT) infection is the leading cause of sexually transmitted disease in the United States and Europe. It is currently estimated that about four million new CT infection occur each year in the United States.

*Chlamydia trachomatis* (CT) is a small obligate intracellular parasite that causes infections in both females and males, adults and newborns. The greatest challenge to the control of CT infection is that as many as 75% of infected women and 50% of infected men are a symptomatic. This results in a large reservoir of unrecognized infected individuals who can transmit the CT infection. The rapid and simple detection of CT infection would greatly assist identification infected individuals.

A) Patient Specimens and sample preparation

Coded samples (207) were obtained from patients with symptoms consistent with CT infection. The cervical samples were collected with a Gen-Probe sample collection kit containing Gen-Probe transport medium; the urine samples were collected into standard urine collection devices. All samples were stored at 4° C.

Cervical swabs were centrifuged at 425×g for 5 minutes to bring all liquid to the bottom of the tube. The swabs were then treated with 40 µl Gen-Probe Specimen Preparation Reagent and incubated at 60° C. for 10 minutes. 20 µl of the treated sample was then pipetted into 400 µl of sample dilution buffer (SDB).

Two ml of each urine sample was warmed to 37° C. for 10 minutes and microfuged at 12,000×g for 5 minutes. The supernatant was discarded and 300 µl of sample dilution buffer was added to each specimen. All 15 serovars of CT were used for inclusive samples, specimens were quantified and 20 µl of specimens containing $4\times10^2$ IFU/ml (inclusion forming unit per ml) of each serovar was added to 400 µl of SDB. A panel of exclusive urogenital micoorganisms was obtained and quantified and 20 µl of $2\times10^9$/ml microorganisms were pipeted into 400 µl of SDB. Positive control containing 0.5 fg rRNA or the equivalent of 0.1 CT elementary body was diluted in SDB.

B) Sample amplificatidin and VIDAS detection

Samples were amplified using the TMA protocol, and rRNA targets were hybridized to oligomer conjugated to AMVE copolymer and an oligomer conjugated to alkaline phosphatase. See for example U.S. Pat. Nos. 5,489,653 and 5,510,084. As described above, the solid phase receptacle (SPR® pipet-like devise) carries the hybrids through successive wash steps and finally into the substrate 4-MUP. The alkaline phosphatase converts the substrate to fluoresence 4-MU, which is detected by the VIDAS assay machine and recorded as relative fluorescence units.

Table 2B below illustrates detection of CT by VIDAS automated assay following amplification as RFV (RFV= RFU - Background RFU) against concentration of CT rRNA. Dilutions of *C. trachomatis* purified rRNA from 0 to 200 molecules were amplified (n=3) and detected in the VIDAS automated probe assay. Detection limit is 20 molecules of purified rRNA.

TABLE 2B

CT Detection by VIDAS

| rRNA Input Molecules | VIDAS RFV |
|---|---|
| 0 | 1 |
| 2 | 121 |
| 20 | 3260 |
| 200 | 8487 |

C) Analytical specificity and Results

Amplifications and detection were carried out in the presence of each of the following ATCC organisms with detections reported as RFV in Table 3 below.

TABLE 3

| Exclusivity panel for CT | | | | |
|---|---|---|---|---|
| Bacillus subtilis 33 | Branhamella catarrhalis 15 | Candida albicans 26 | Chlamydia pneumoniae 39 | Chlamydia psittaci 11 |
| Escherichia coli 11 | Klebsiella pneumoniae 13 | Lactobacillus acidophilus 27 | Neisseria elongata 44 | Neisseria lactamica 18 |
| Neisseria meningitidis-D 61 | Neisseria meningitidis-Y 52 | Propionibacterium acnes 14 | Pseudomonas aeruginosa 13 | Staphylococcus aureus 13 |
| Streptococcus agalactiae 16 | Streptococcus bovis 45 | Streptococcus pneumoniae 34 | Yersinia enterolitica 11 | Chlamydia trachomatis 10673 |
| Negative Control 12 | | | | |

Analytical specificity for Chlamydia serovars data reported as RFV is shown in Table 4 below.

TABLE 4

| Inclusivity Panel for CT | | | | |
|---|---|---|---|---|
| Serovar A | Serovar B | Serovar Ba | Serovar C | Serovar D |
| 5421 | 7247 | 9626 | 8066 | 10849 |

TABLE 4-continued

Inclusivity Panel for CT

| Serovar E 4608 | Serovar F 9916 | Serovar G 10082 | Serovar H 7769 | Serovar I 9733 |
|---|---|---|---|---|
| Serovar J 9209 | Serovar K 2423 | Serovar L1 10786 | Serovar L2 1812 | Serovar L3 5883 |
| Positive Control 3775 | Negative Control 9 | | | |

Table 5 below illustrates the results of clinical cervical swab specimen testing for CT comparing results from the Gen-Probe manual AMP-CT assay and the VIDAS automated probe assay.

TABLE 5

Amplified Clinical Cervical Specimen Detection of CT

| | | Gen-Probe manual AMP-CT assay | |
|---|---|---|---|
| | | + | − |
| VIDAS off-line automated probe assay | + | 35 | 0 |
| | − | 0 | 85 |

Table 6 below illustrates the results of clinical urine specimen testing comparing the results of manual AMP-CT assay and the VIDAS automated probe assay.

TABLE 6

Amplified Clinical Urine Specimen detection of CT

| | | Gen-Probe manual AMP-CT assay | |
|---|---|---|---|
| | | + | − |
| VIDAS off-line automated probe assay | + | 25 | 0 |
| | − | 0 | 62 |

Thus there was perfect agreement in assay results between the automated probe assay using the VIDAS instrument and the manual Gen-Probe AMP-CT assay.

EXAMPLE 5

Multiplex (Multiple Sequence) Nucleic Acid Detection

The value of diagnostic tests based on nucleic acid probes can be substantially increased through the detection of multiple different nucleic acid targets, and the use of internal positive controls. An automated method has been devised for use with the VIDAS instrument (BioMérieux Vitek, Inc.) which can discretely detect at least two different nucleic acid target sequences in one assay reaction, and is termed the Multiplex protocol. Thus a nucleic acid amplification procedure, or a processed test sample may be screened for more than one amplified nucleic acid target in the same assay. This method relies on the spatial separation of discrete nucleic acid probes which can capture different target nucleic acid sequences, on the Solid Phase Receptacle (SPR® pipet-like devise) of the VIDAS instrument. The SPR® is a disposable pipet-like tip which enables fluid movements as well as acting as the solid support for affinity capture. The multiplex capture by SPR® is demonstrated using capture probes specific for *Chlamydia trachomatis* (CT) and *Neisseria gonorrhoeae* (AG).

Figure 15:
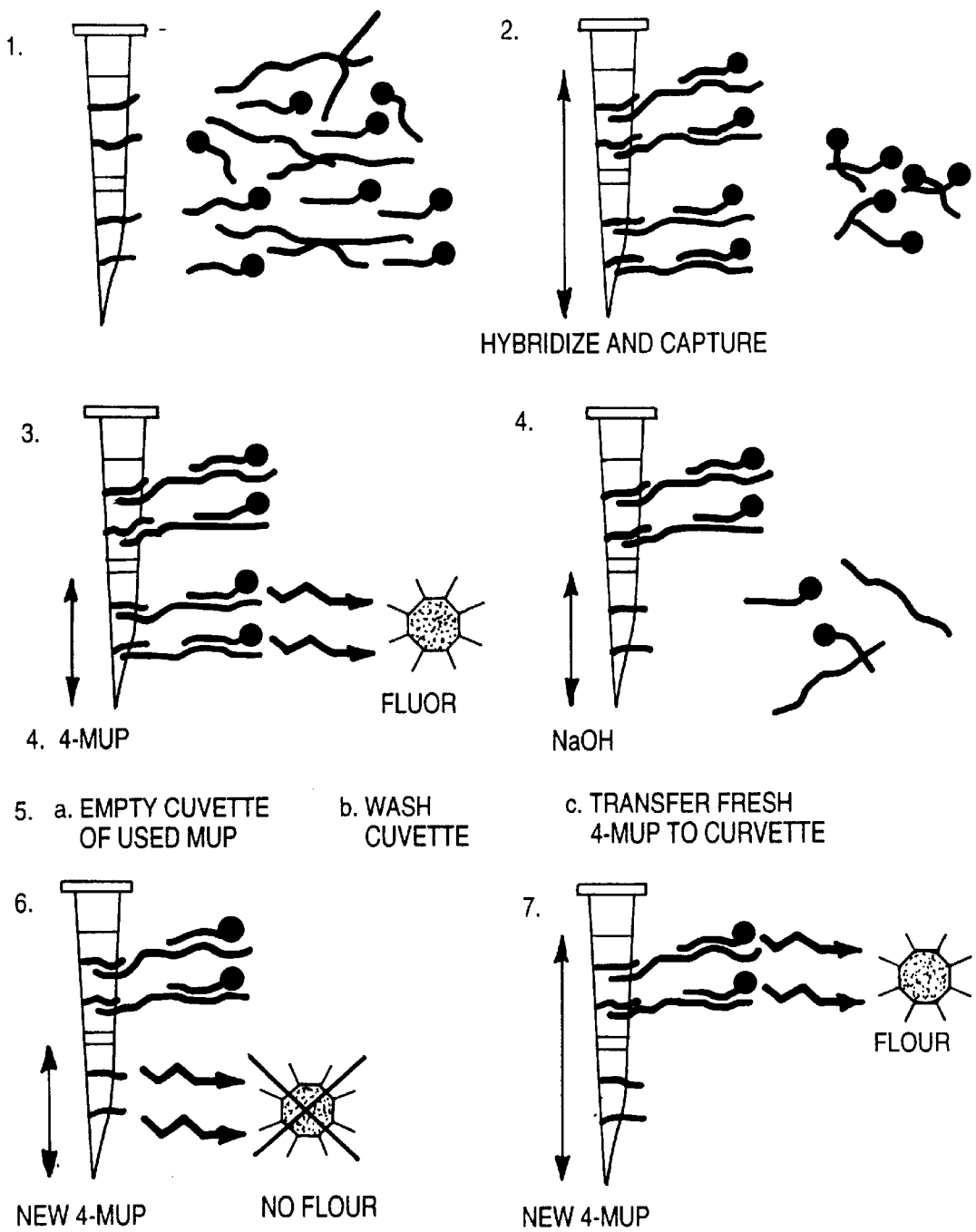
FIG. 15 illustrates a schematic of the operation of the multiplex VIDAS detection.

FIG. 15 illustrates a schematic of the operation of the multiplex VIDAS detection. Solid phase receptacles (SPR® pipet-like devise) are coated with two distinct zones of oligonucleotides with nucleic acid sequences which are used to specifically capture target nucleic acid sequences with their corresponding specific reporter probe nucleic acids labeled with alkaline phosphatase (AKP). Following washes to remove unbound reporter probes, AKP localized to the SPR® bottom is detected with the fluorescent substrate 4-MUP. The AKP is stripped from the bottom of the SPR® with NaOH. The enzyme reaction well is emptied, washed, and re-filled with fresh 4-MUP. To ensure the removal of AKP from the bottom of the SPR® the new substrate is exposed to the bottom of the SPR® and residual fluorescence is measured. Finally, target bound to the top of the SPR® is detected by inmmersing the SPR® in the 4-MU).

Figure 16:
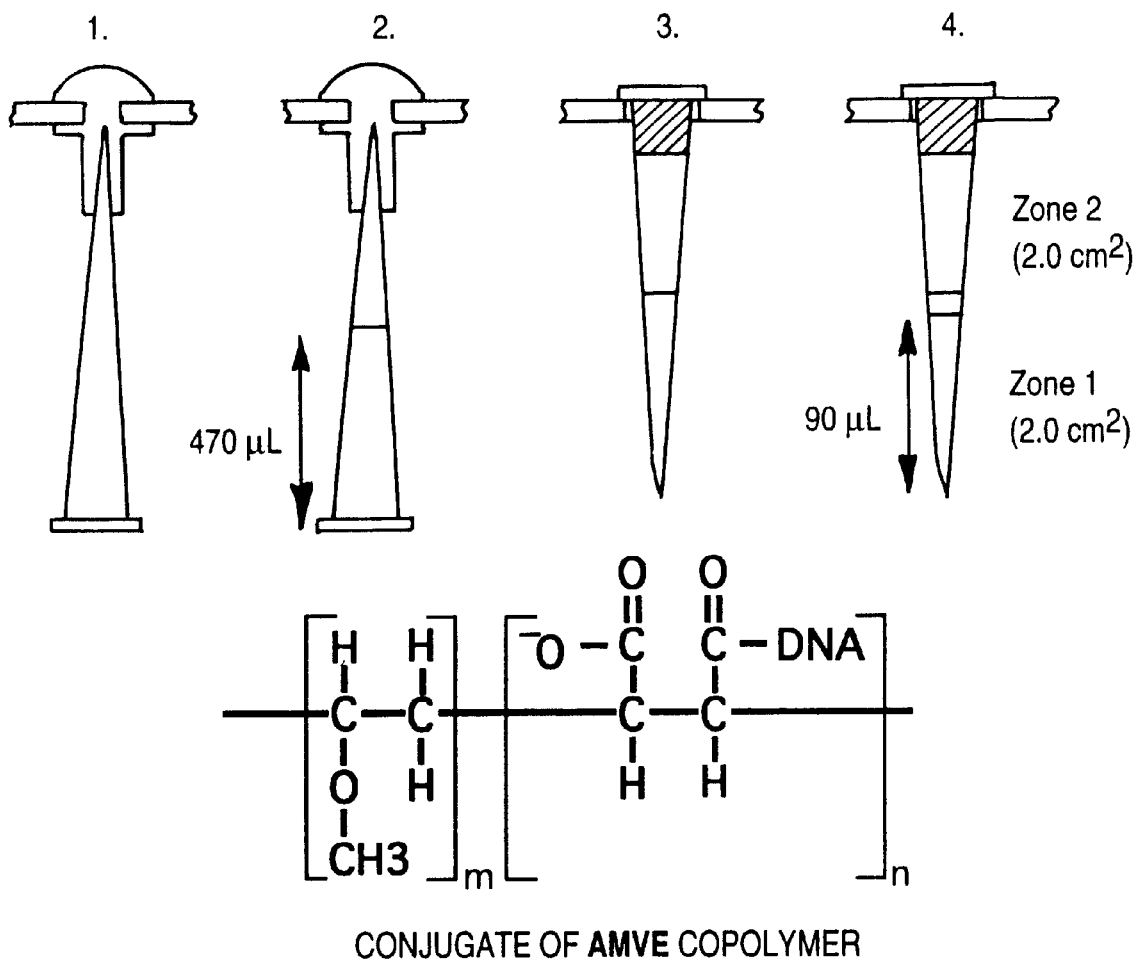
FIG. 16 illustrates the production of SPR® with two distinct capture zones.

FIG. 16 illustrates the production of SPR® with two distinct capture zones. The SPR® is inserted tip-first into a silicon plug, which are held in a rack. Differential pressure is used to uniformly draw a 1 µg/ml solution of a specific capture probe, conjugated to AMVE copolymer, into all SPR®s at one time. Attachment of the conjugate to the SPR® surface is activated by passive adsorption for several hours at room temperature. After washing, and drying, the SPR®s are capped with a small adhesive disc and inserted into new racks in a tip-down orientation. The lower portion of the SPR® is then similarly coated with a second capture probe conjugate. SPR®s are stable when stored dry at 4° C.

Figure 17:
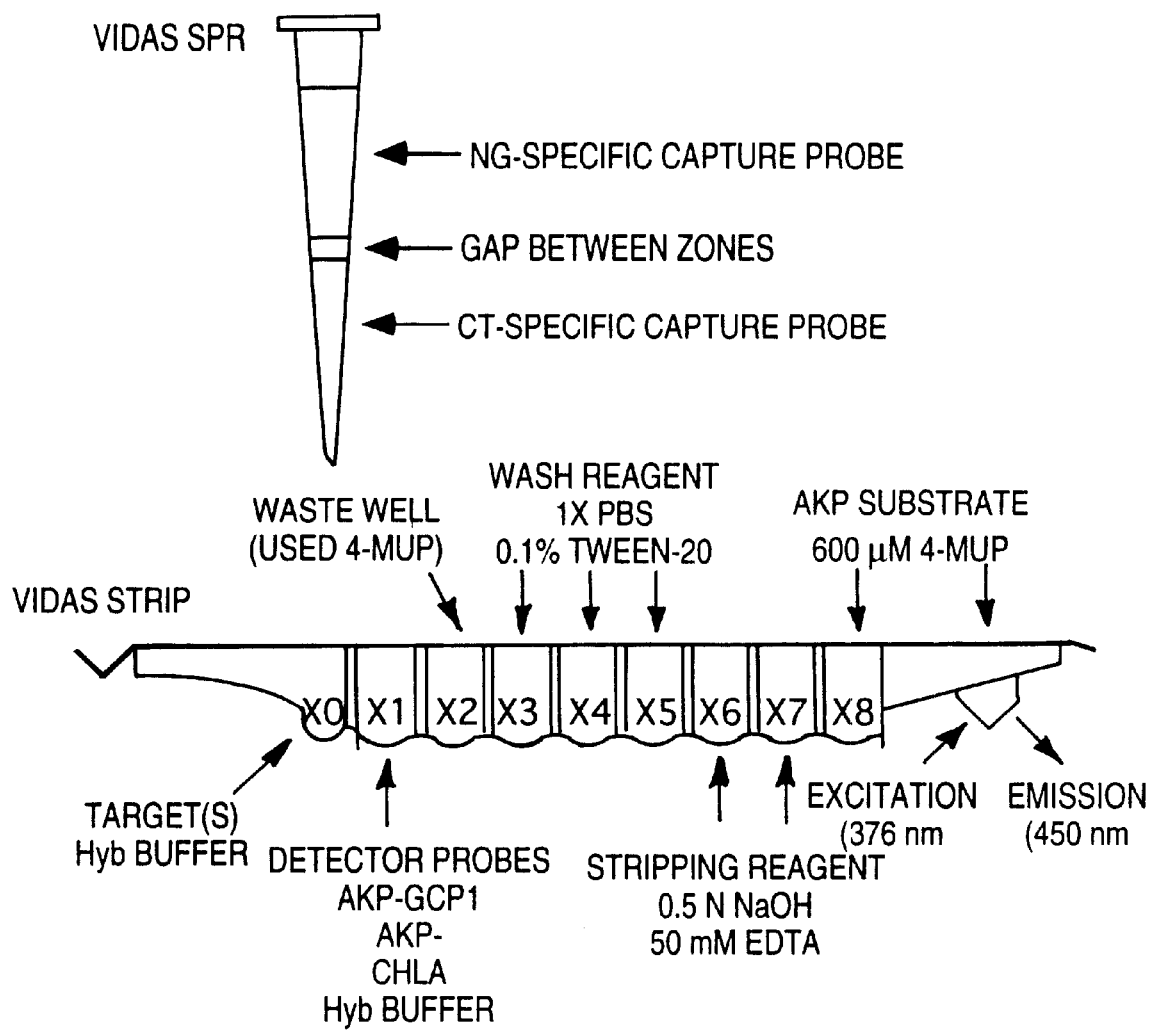
FIG. 17 illustrates the VDAS apparatus strip configuration for multiplex detection.

FIG. 17 illustrates the VIDAS apparatus strip configuration for multiplex detection. The strip can be pre-filled with 200 µl of AKP-probe mix (about $1\times10^{12}$ molecules each) in hybridization buffer in well X1, 600 µl of wash buffer in wells X3, X4, X5, 600 µl of stripping reagent in wells X6 and X7, and 400 µl of AKP substrate in X8 and sealed with foil. A foil-sealed optical cuvette (XA) containing 300 µl of 4-MUP is snapped into the strip, and the strips are inserted into the VIDAS instrument at 37° C. The multiplex VIDAS protocol is then executed using SPR®s coated with two capture probes in distinct zones.

The VIDAS multiplex protocol can involve many steps. For example the validation test protocol contained 13 steps as follows:

1. Transfer of 203 µl target from X0 to AKP-probes in X1,
2. Hybridize and capture to SPR®,
3. Wash SPR® (316 µl) twice with PBS/Tween (X3, X4),
4. 4-MUP to SPR® bottom (89.6 µl) in XA for 5.3 minutes then read,
5. 4-MUP to SPR® bottom (89.6 µl) in XA for 14.8 minutes then read,
6. Transfer used substrate from XA to X2 (5×67.1 µl),
7. Strip AKP from SPR® bottom (1 12.6 µl) with NaOH (X7),
8. Wash XA with fresh NaOH (3×112.6 µl; X6 to XA to X6),
9. Wash XA with PBS/Tween (3×112.6 µl; X5 to XA to X5),
10. Transfer fresh 4-MUP from X8 to XA (6×48 µl),
11. 4-MUP to SPR® bottom (89.6 µl) in XA for 10.7 minutes then read,
12. 4-MUP to SPR® top (294 µl) in XA for 5.5 minutes then read,
13. 4-MUP to SPR® top (294 µl) in XA for 15 minutes then read.

Hybridization, substrate, wash and stripping steps all involve multiple cycles of pipeting the respective solution into the SPR®, holding the solution for a defined period of time, and pipeting the solution out of the SPR®. Hold times for hybridization, substrate and washing or stripping are 3.0, 0.5 and 0.17 minutes respectively. "Read" means the fluorescence is detected by the apparatus. Total assay time for the research protocol was about 1.75 hours but can be reduced to 75 minutes.

Figure 18:
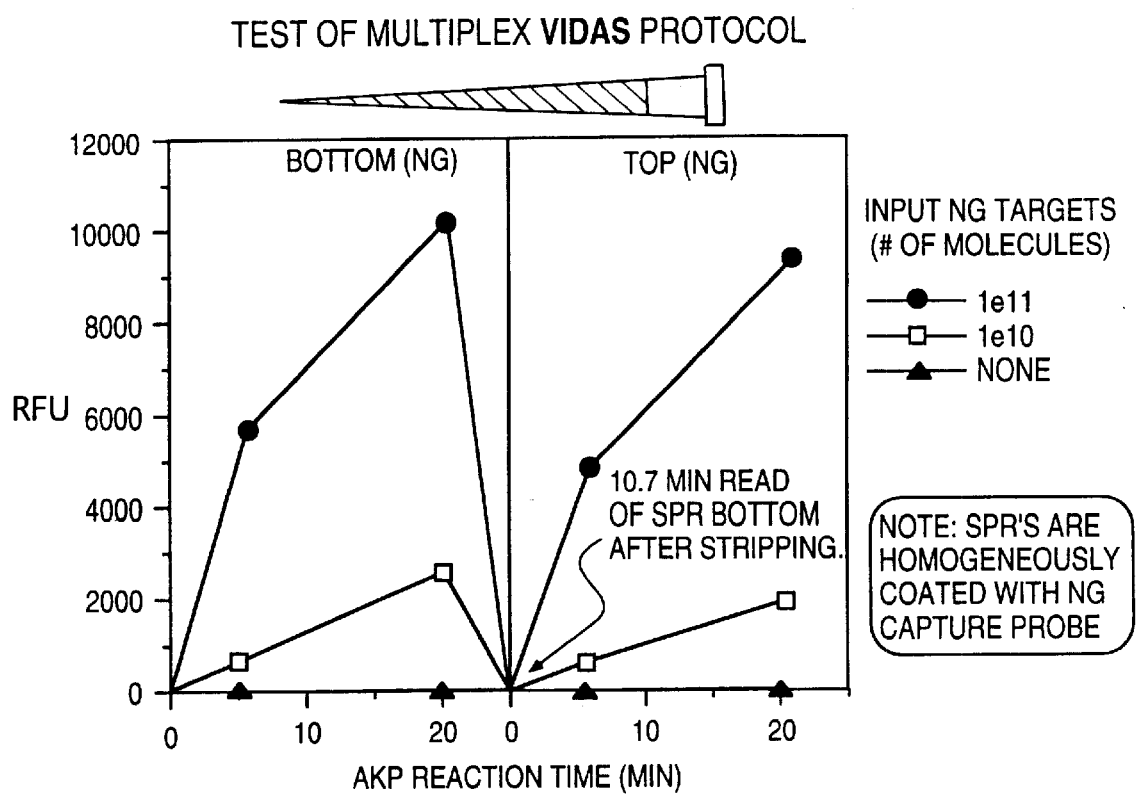
FIG. 18 illustrates and graphs the results of verification of the VIDAS multiplex protocol detecting only NG target.

FIG. 18 illustrates and graphs the results of verification of the VIDAS multiplex protocol executed as described above, wherein the SPR® was homogeneously coated with only a single capture probe for Neisseria gonorrhoeae (NG). The number of NG oligonucleotide targets in the test sample was varied from 0, $1\times10^{10}$, or $1\times10^{11}$ molecules in the test sample. The data shown are averages of replicate samples. The graph as illustrated is divided into two parts; the left and right halves show the results of two fluorescent measurements from the lower and the upper zones of the SPR®, respectively. The measurements taken from the bottom zone after stripping the lower area of bound nucleic acid, and exposure for about 11 minutes in fresh 4-MUP substrate was approximately 46 RFU for all samples tested, and was equivalent to background fluorescence measured. This measurement is shown by the 0 time point in the center of the graph. Thus the graph illustrates two sequential sets of measurements of fluorescence from a single SPR®, the first set of measurements being taken from the bottom half of the SPR® (left half of the graph), and a second set of measurements taken from the top of the SPR® (the right of the graph).

Figure 19A:
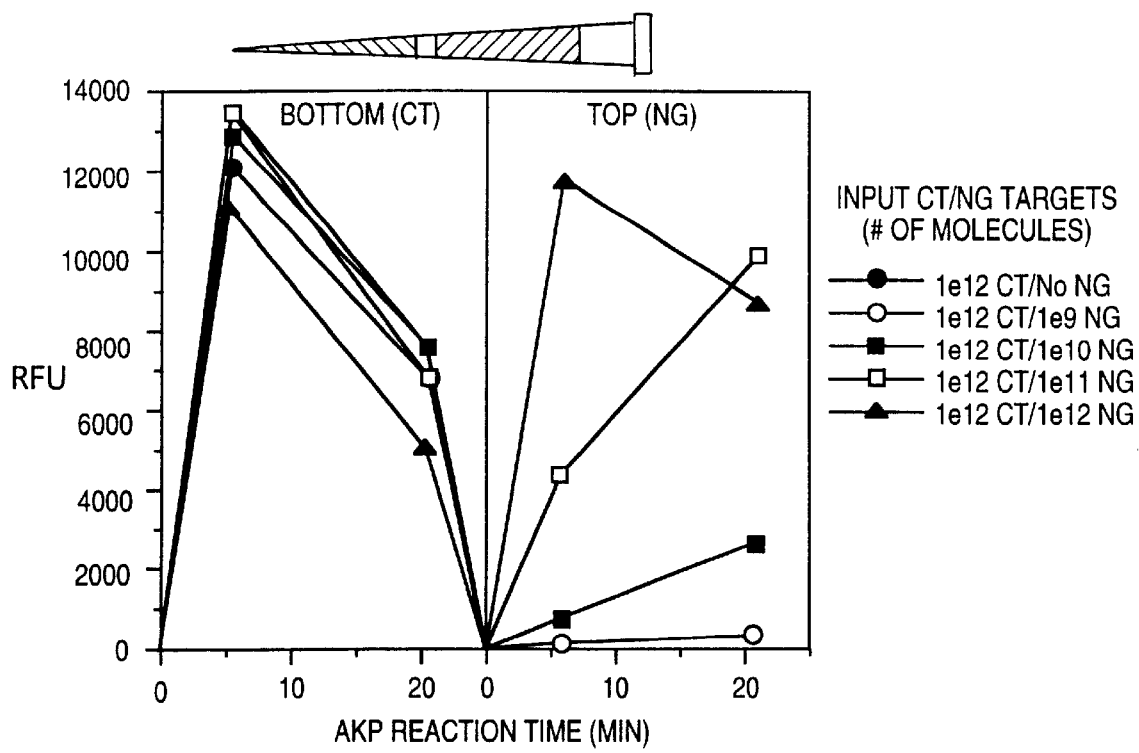
FIG. 19A/46A is a graph showing the results when $1\times10^2$ CT targets were mixed with 0, $1\times10^9$, $1\times10^{10}$, $1\times10^{11}$, or $1\times10^{12}$, NG targets, and detected with the VIDAS instrument using the multiplex protocol and SPR®s coated with CT capture probes on the bottom zone of the SPR®, and NG capture probes on the top zone of the SPR®.
Figure 19B:
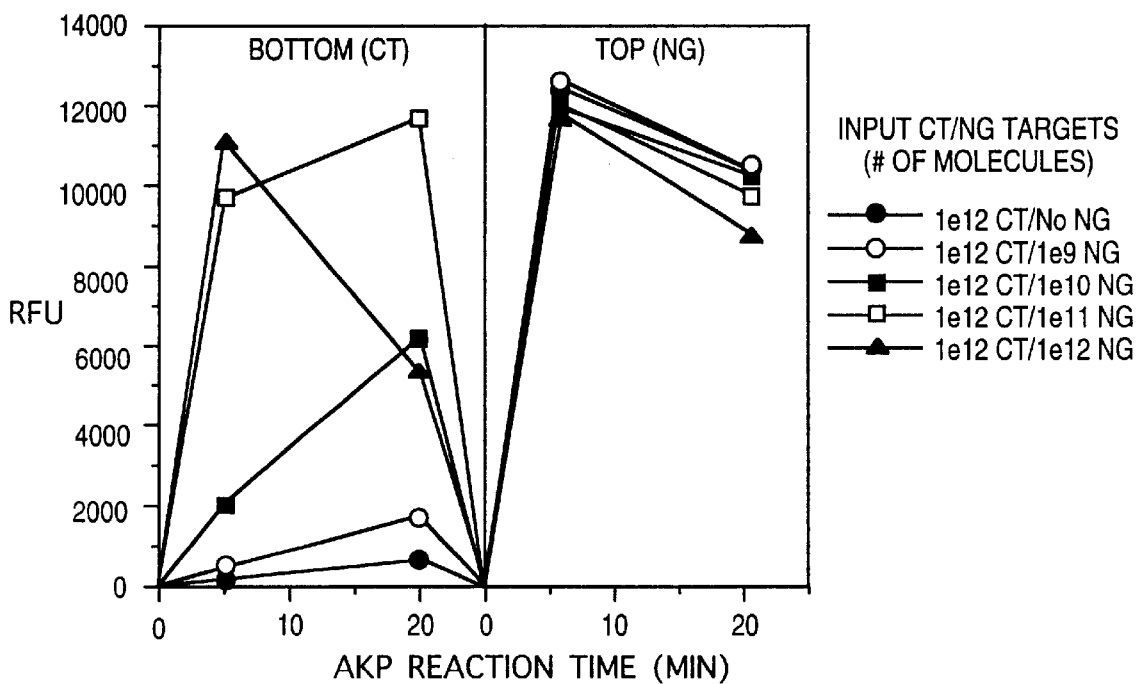
FIG. 19B/46B illustrates the results when $1\times10^{12}$ NG targets was mixed with 0, $1\times10^9$, $1\times10^{10}$, $1\times10^{11}$, or $1\times10^{12}$, NG targets, and detected with the VIDAS instrument using the multiplex protocol and SPR® coated with CT capture probes on the bottom zone of the SPR®, and NG capture probes on the top zone of the SPR®.

FIG. 19 illustrates Multiplex detection of CT and NG oligonucleotide targets at different input amounts. FIG. 19A is a graph showing the results when $1\times10^{12}$ CT targets were mixed with 0, $1\times10^9$, $1\times10^{10}$, $1\times10^{11}$, or $1\times10^{12}$, NG targets, and detected with the VIDAS instrument using the multiplex protocol and SPR®s coated with CT capture probes on the bottom zone of the SPR®, and NG capture probes on the top zone of the SPR®. FIG. 19B illustrates the results when $1\times10^{12}$ NG targets was mixed with 0, $1\times10^9$, $1\times10^{10}$, $1\times10^{11}$, or $1\times10^{12}$, CT targets, and detected with the VIDAS instrument using the multiplex protocol and SPR®s coated with CT capture probes on the bottom zone of the SPR®, and NG capture probes on the top zone of the SPR®. The data is graphed as above where the graph illustrates two sequential sets of measurements of fluorescence from a single SPR®, the first set of measurements being taken from the bottom half of the SPR® (left half of the graph), Stripped and verified (the center of the graph) and a second set of measurements taken from the top of the SPR® (the right of the graph).

Table 7 below summarizes the data obtained by Multiplex VIDAS detection of CT and NG in a sample at various target levels, reported in RFUs.

TABLE 7

Detection of CT and NG targets in sample

| RFUs[A] | none[B] | $1 \times 10^9$ | $1 \times 10^{10}$ | $1 \times 10^{11}$ | $1 \times 10^{12}$ | $1 \times 10^{13}$ |
|---|---|---|---|---|---|---|
| none[C] | 43[D]/<br>40[E] | 43/<br>116 | 46/<br>693 | 62/<br>7116 | 174/<br>11817 | 273/<br>12136 |
| $1 \times 10^9$ | 189/<br>41 | 246/<br>118 | 169/<br>773 | 220/<br>5750 | 422/<br>12522 | 399/<br>11401 |
| $1 \times 10^{10}$ | 1736<br>41 | 2258/<br>125 | 1937/<br>734 | 1931/<br>6639 | 2128/<br>12390 | 2371/<br>11180 |
| $1 \times 10^{11}$ | 10339/<br>48 | 9815/<br>145 | 9858/<br>760 | 9369/<br>4571 | 9784/<br>11825 | 10252/<br>10312 |
| $1 \times 10^{12}$ | 12149/<br>49 | 13520/<br>148 | 12940/<br>796 | 13593/<br>4397 | 11239/<br>11786 | 10158/<br>9900 |
| $1 \times 10^{13}$ | 11545/<br>57 | 11713/<br>121 | 10804/<br>815 | 12805/<br>5404 | 12305/<br>12326 | 11416/<br>10490 |

[A]Data is reported in RFUs, after ~5 minute exposure of 4-MUP to bound AKP-probe
[B]Columns are data for that number of NG targets in sample
[C]Rows are the data for that number of CT targets in sample
[D]The first value reported is RFU detected from the CT assay portion
[E]The second value reported is RFU detected from the NG assay portion Thus the multiplex VIDAS protocol is clearly operative and enables the rapid and discrete detection of more than one different nucleic acid signal in a sample. This protocol, and the SPR® coating can be manipulated in many formats to present coating zones of different surface area with different sized gaps between detection zones. The SPR® can be coated with nucleic acids which are designed to capture different regions of the same nucleic acid sequence to detect, for example, truncated gene expression, different alleles or alternatively spliced genes. The SPR® can be coated to capture internal control nucleic acid sequences which can be used to detect and confirm successful nucleic acid amplification reactions. Thus the VIDAS protocol is a flexible method for detection of more than one nucleic acid sequence in the same sample, in a single assay.

EXAMPLE 6

Internal Control Sequence and Method

The construction of internal control sequences composed of functional building blocks of sequences chosen by random generation of nucleic acid sequences for use as amplification reaction internal positive controls ideally requires that the control sequences be specifically designed to be used for the various nucleic acid amplification protocols including but not limited to PCR, LCR, TMA, NASBA, and SDA. The internal control nucleic acid sequence, in combination with the appropriate sequence specific oligonucleotide primers or promoter-primers will generate a positive amplification signal if the amplification reaction was successfully completed.

Ideally, the internal control nucleic acid is useful regardless of the nucleic acid sequences present in the target organism, the host organism, or nucleic acids present in the normal flora or in the environment. Generally, the internal control sequences should not be substantially similar to any nucleic acid sequences present in a clinical setting, including human, pathogenic organism, normal flora organisms, or environmental organisms which could interfere with the amplification and detection of the internal control sequences.

The internal control sequences of the instant invention are comprised of functional blocks of sequences chosen from a list of randomly generated nucleic acid sequences. The functional blocks are segments which provide for a special property needed to allow for amplification, capture, and detection of the amplification product. For example, in a TMA reaction, the internal control sequences are most useful when the functional blocks meet certain functional requirements of the amplification protocol, such as: a) a primer binding site on the anti-sense strand; b) a capture site;

c) a detector probe binding site; d) a T7-promoter containing primer binding site on the sense strand. Each of these functional elements has its own particular constraints, such as length, %G-C content, Tm, lack of homology to known sequences, and absence of secondary structural features (i.e. free from dimer formation or hairpin structures) which can be used to select the appropriate sequence. Thus randomly generated functional blocks of sequences can be screened for the desired functional properties before use in constructing internal control sequences.

In order to construct a internal control sequences having the desired properties comprising a specified number of functional blocks and satisfying the desired constraints within each block, a random sequence generator was used to generate strings of numbers; each number being limited to the range from 0.000 to 4.000. The length of the strings is flexible and chosen based upon the desired lengths of the functional blocks.

Each number in the string (i.e. n1, n2, n3, n4 . . . nx where x is the length of the string) was then assigned a corresponding nucleotide as follows: guanosine (G) if $0<n\leq1$; adenosine (A) if $1<n\leq2$; thymidine (T) if $2<n\leq3$; and cytosine (C) if $3<n\leq4$. A large collection of such strings was produced and screened for those meeting the sequence and structural requirements of each functional block. FIG. 23 illustrates the results generated by the method described showing a collection of strings of nucleic acid sequences and screening for specific functional parameters.

Potential internal control (IC) sequences were then constructed by assembling the functional blocks (selected at random) in the proper order. Finally, the assembled internal control sequences were then examined to insure that overall sequence and structural constraints were maintained. For example, in a TMA internal control sequence the two primer binding sites should not have a significant base-pairing potential or form stable 3' dimer structures. Those internal control sequences which pass thorough these layers of screening were then physically produced using overlapping oligonucleotides and tested for performance in actual amplification/detection assays.

Although any one function block may have some homology to sequences present in a clinical setting (a perfect match of 21 nucleotide block is expected at a random frequency of 1 in every 4e12 sequences or about $4 \times 10^{21}$; generated sequences were screened against GenBank data base) it is highly unlikely that all functional blocks will be found to have substantial homology. Since the internal control nucleic acid sequences are constructed of a group of functional blocks placed in tandem, the chance possibility that a natural nucleic acid sequence will have an identical string of nucleic acid sequence blocks in the same tandem organization is remote.

Figure 25:
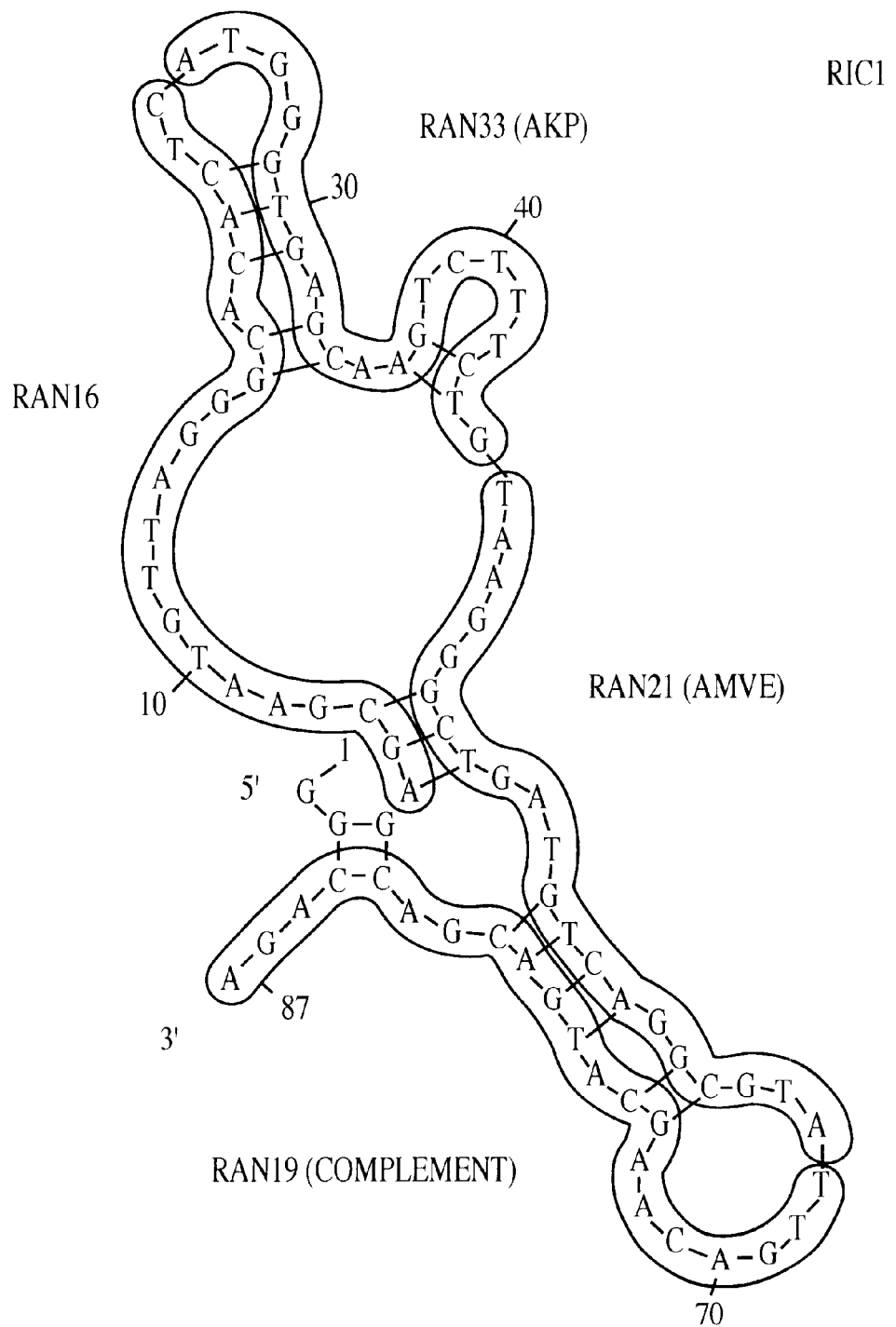
FIG. 25 shows an analysis of the possible secondary structural components of the RIC 1 sequence (SEQ ID NO:37).

Two specific internal control sequences have been constructed using the method described above. Random Internal Control 1 (RIC1) is shown in FIG. 24 with the possible oligonucleotide primers/probes for amplification and detection of the control sequence. FIG. 25 shows an analysis of the possible secondary structural components of the RIC1 sequence. RIC1 was constructed using randomly generated strings ran16, ran19, ran21 and ran33. The functional blocks requiring primer binding were met by ran16 and ran19, while the capture site was satisfied by ran21 and the detector probe binding site was met by ran33.

Figure 26:
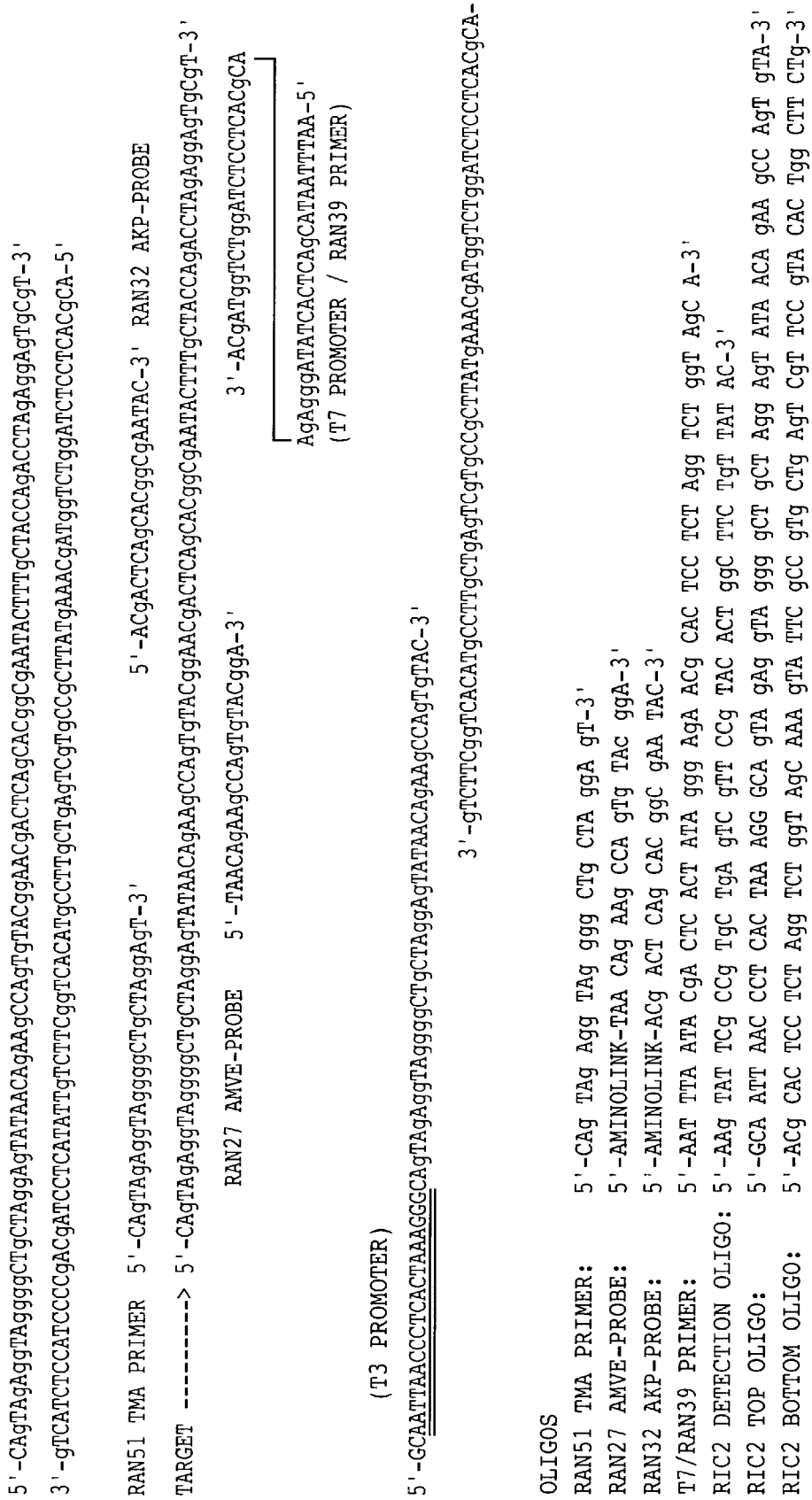
FIG. 26 shows the nucleic acid sequence of Random Internal Control 2 (RIC2) with the possible oligonucleotide primers/probes for amplification and detection of the control sequence.
Figure 27:
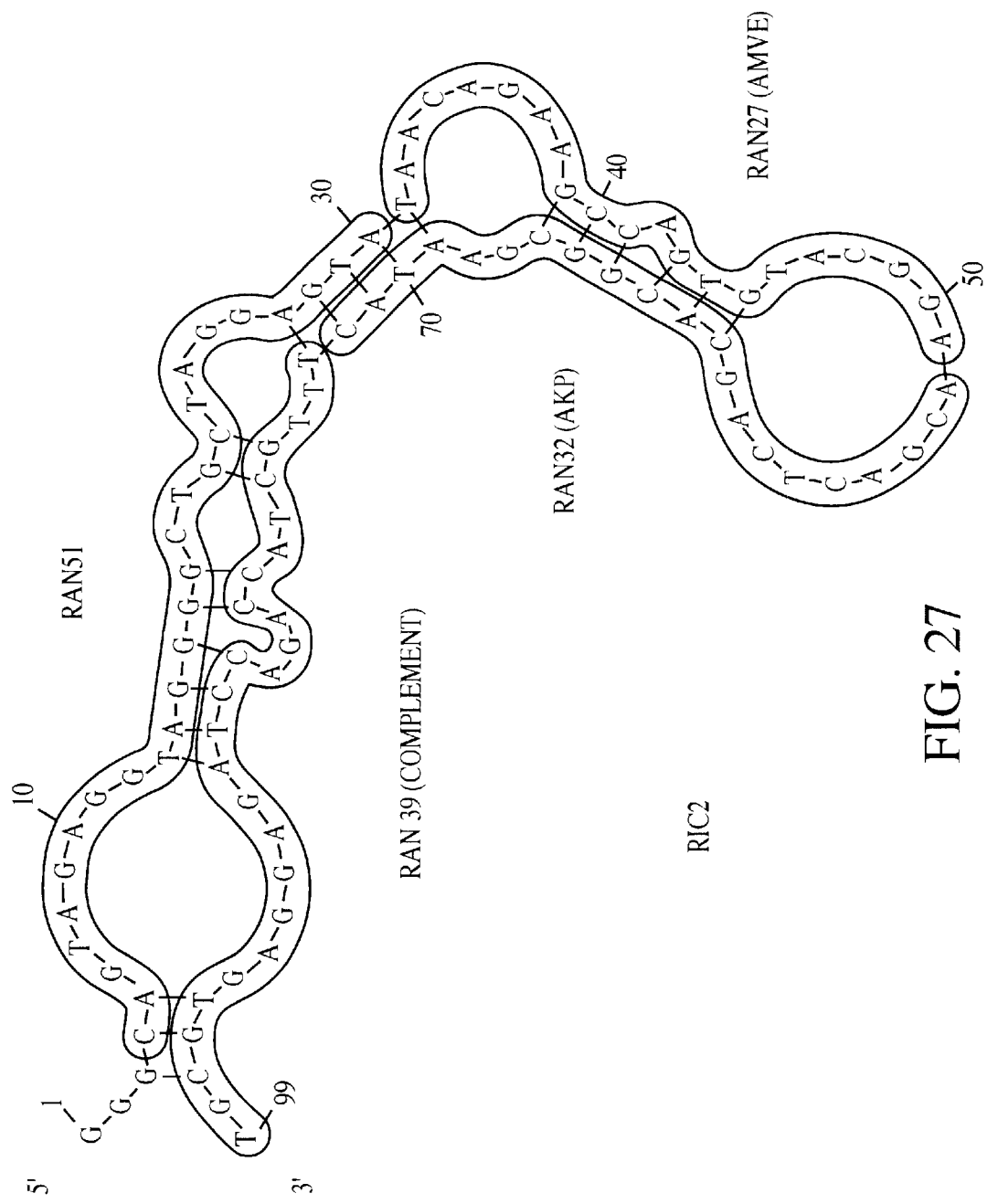
FIG. 27 shows an analysis of the possible secondary structural components of the RIC2 sequence (SEQ ID NO:44).
Figure 28:
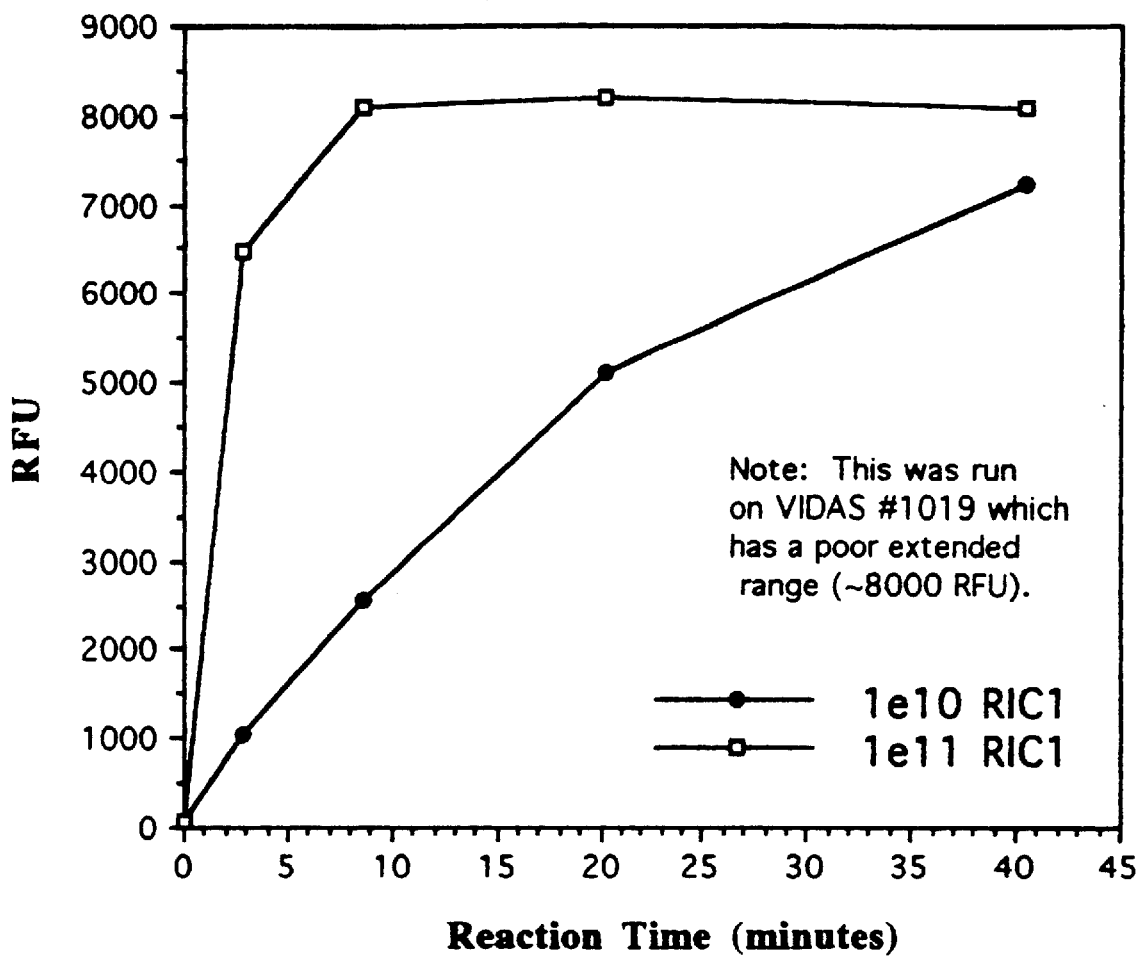
FIG. 28 illustrates results from detection of RIC1 DNA, where the ran21 was the capture probe and ran33 was an enzyme-linked detector-probe, and shows that amplification and detection occurs under standard assay conditions.

Random Internal Control 2 (RIC2) is shown in FIG. 26 with the possible oligonucleotide primers/probes for amplification and detection of the control sequence. FIG. 27 shows an analysis of the possible secondary structural components of the RIC2 sequence. Similarly to RIC1, RIC2 was constructed using randomly generated strings ran27, ran32, ran39 and ran51. Thus, illustrating that it is also possible that the functional blocks requiring primer binding, capture site, detector probe binding site can be met by alternative random sequences generated by the method described above. FIG. 28 illustrates results from detection of RIC1 DNA, where the ran21 was the capture probe and ran33 was an enzyme-linked detector-probe, and shows that detection occurs under standard assay conditions with expected fluorescence intensities. FIG. 29 shows that RIC1 RNA, amplified by TMA and detected on a VIDAS instrument (BioMérieux Vitek, Inc.) using the enzyme-linked detection system, has a limit of sensitivity of about 1000 molecules of RIC1 RNA (without optimization of conditions). Similar analysis of RIC2 sequences was performed and found to be similar to RIC1. It is significant that the amplification and detection system of the internal control functioned effectively under the conditions optimized for the selected target.

As an alternative approach for multiplex detection using internal controls (IC), SPR®s can be homogeneously coated with a mixture of different capture nucleic acid sequences in a single, whole-SPR® zone. For example, two capture nucleic acid sequences can be combined in one zone, one specific for a target test sequence, and one specific for an internal control sequence. Target amplicons, if present, and internal control amplicons are simultaneously hybridized to the SPR® by the capture probes. In the presence of labeled probe nucleic acid sequences specific for the target test nucleic acid sequence. Following washing, a first read is done to so that the presence or absence of label on the SPR® is determined to ascertain the presence of the test target. A second hybridization is then done (sequential hybridization) to the SPR® using a detection label nucleic acid sequence specific for the internal control. The SPR® is washed to remove excess unbound detection probe, and the second label is measured to indicate the presence or absence of the internal control. If the first signal is negative, a positive signal from the IC second read confirms the functionality of the amplification/detection system. In this case, one can conclude that the test target nucleic acid sequence was truly absent (true negative). If the first signal is positive, this alone is enough to confirm functionality of the amplification and detection system, and the second signal is immaterial (positive result). In the special case where the first the first and second label are the same, an additive signal will result from the positive first read and the positive second IC read. If both the first signal is negative and the second IC signal is also negative, then the amplification/detection functionality failed, which could be due to for example, sample interference or mechanical failure. In this case the test result is reported invalid (false negative) and re-testing is recommended.

There is great interest in the use of internal controls, the underlying rational being that ". . . if the sample will not support the amplification of the internal control, it is unlikely to support the amplification of the target nucleic acid sequence." (NCCLS Document MM3-A, Molecular Diagnostic Methods for Infectious Diseases; Approved Guideline, p. 55, March 1995).

Using a sequential. hybridization approach with multiple detector probes, it has been possible to design protocols which allow for the discrete detection of first read signal (ie.

pure CT signal) and an additive "mixed" second read (ie. additive CT and discrete signal for negatives; see Table 7A below). This protocol will not need stripping with NaOH. For example, Table 7A shows the results when different mixtures of synthetic targets were first captured with homogeneously coated SPR®s (CT and IC capture probes) and hybridized with the CT detector probe. After the first read, hybridization was performed with the IC detector probe, followed by a second read (same substrate).

This type of protocol can also be used for a combined Gc/CT/internal control assay, if a screening approach is allowed (no discrimination between GC and/or CT positives during the first read). GC and CT specific signals have to be resolved by running the CT and GC specific assays on screen positive samples (5–10% of cases, depending on prevalence) SPR®s would be coated homogeneously with 3 capture probes (CT/GC/internal control).

TABLE 7A

Homogeneous Coated SPR ® Detection of multiple signals

| Target | CT 1$^{st}$ Read | IC 2$^{nd}$ Read | Bkg.RFU |
|---|---|---|---|
| 10$^{10}$ CT | 7077 | 8608 | 58 |
| 10$^{10}$ IC | 58 | 4110 | 56 |
| 10$^{10}$ IC/CT | 5594 | 8273 | 57 |
| 10$^{10}$ IC/CT | 5712 | 8317 | 57 |
| no target | 66 | 89 | 57 |

Thus internal control sequences described above are useful for application with VIDAS apparatus with coated SPR® and the use of the Multiplex system to provide for combined assay detection of a nucleic acid and monitoring control for successful reaction.

We claim:

1. A universal positive amplification internal control nucleic acid having the nucleic acid sequence of RIC1 (SEQ ID NO:37).

2. A universal positive amplification internal control nucleic acid having the nucleic acid sequence of RIC2 (SEQ ID NO:44).

* * * * *